(12) United States Patent
Tso et al.

(10) Patent No.: US 6,635,226 B1
(45) Date of Patent: Oct. 21, 2003

(54) MICROANALYTICAL DEVICE AND USE THEREOF FOR CONDUCTING CHEMICAL PROCESSES

(75) Inventors: Jacqueline Tso, Fremont, CA (US); Sally A. Swedberg, Palo Alto, CA (US); Paul K Wolber, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/502,593

(22) Filed: Feb. 11, 2000

Related U.S. Application Data

(63) Continuation-in-part of application No. 08/656,281, filed on Apr. 27, 1998, now Pat. No. 6,033,628, which is a continuation-in-part of application No. 08/482,245, filed on Jun. 7, 1995, now Pat. No. 5,658,413, which is a continuation-in-part of application No. 08/326,111, filed on Oct. 19, 1994, now Pat. No. 5,500,071.

(51) Int. Cl.[7] .............................................. B01J 10/00
(52) U.S. Cl. ..................... 422/129; 422/198; 422/199; 422/307; 435/283.1
(58) Field of Search ................................ 422/129, 198, 422/199, 307; 435/283.1

(56) References Cited

U.S. PATENT DOCUMENTS

| | | | |
|---|---|---|---|
| 4,683,195 A | 7/1987 | Mullis et al. ................... 435/6 |
| 4,683,202 A | 7/1987 | Mullis ......................... 435/91.2 |
| 4,800,159 A | 1/1989 | Mullis et al. ............... 435/91.2 |
| 4,891,120 A | 1/1990 | Sethi et al. ................... 204/600 |
| 4,908,112 A | 3/1990 | Pace ......................... 204/601 X |
| 4,965,188 A | 10/1990 | Mullis et al. ................... 435/6 |
| 5,132,012 A | 7/1992 | Miura et al. .............. 210/198.2 |
| 5,194,133 A | 3/1993 | Clark et al. ................... 204/608 |
| 5,291,226 A | 3/1994 | Schantz et al. ............... 347/63 |
| 5,305,015 A | 4/1994 | Schantz et al. ................ 347/47 |
| 5,333,675 A | 8/1994 | Mullis et al. ................ 165/268 |
| 5,587,128 A | * 12/1996 | Wilding et al. ................ 422/50 |
| 5,639,423 A | * 6/1997 | Northrup et al. .............. 122/50 |
| 5,656,493 A | 8/1997 | Mullis et al. ............. 435/286.1 |
| 6,132,580 A | * 10/2000 | Mathies et al. .............. 204/453 |
| 6,180,372 B1 | * 1/2001 | Franzen ...................... 435/91.1 |

OTHER PUBLICATIONS

Fan et al. (1994), "Micromachining of Capillary Electrophoresis Injectors and Separators on Glass Chips and Evaluation of Flow at Capillary Intersections," *Analytical Chemistry* 66(1):177–184. Jan. 1, 1994.
Harrison et al. (1993), "Towards Miniaturized Electrophoresis and Chemical Analysis Systems on Silicon: An Alternative to Chemical Sensors," *Sensors and Actuators B,* 10(2):107–116. No Date.
Manz et al. (1990), "Design of an Open–Tabular Column Liquid Chromatograph Using Silicon Chip Technology," *Sensors and Actuators B1*:249–255. (1990).
Manz et al. (1991), Micromachining of Monocrystalline Silicon and Glass for Chemical Analysis Systems, *Trends in Analytical Chemistry* 10(5):144–149. (1991).
Manz et al. (1993), "Planar Chips Technology for Miniaturization of Separation Systems: A Developing Perspective in Chemical Monitoring," *Adv. in Chrom. 33*:1–66. No Date.

* cited by examiner

*Primary Examiner*—Nam Nguyen
*Assistant Examiner*—John S. Starsiak, Jr.

(57) ABSTRACT

A microanalytical device is provided for conducting chemical processes using small amounts of fluid. The devices include microstructures, e.g., microcavities, microchannels and the like, that are laser ablated or otherwise formed in a support substrate, and can be used in a variety of chemical and biochemical methods, including chromatographic, electrophoretic and electrochromatographic separations, screening and diagnostics, and chemical and biochemical synthesis. The devices are formed from a material that is thermally and chemically stable and resistant to biofouling, significantly reducing electroosmotic flow and unwanted adsorption of solute. Preferred materials are polymeric.

20 Claims, 20 Drawing Sheets

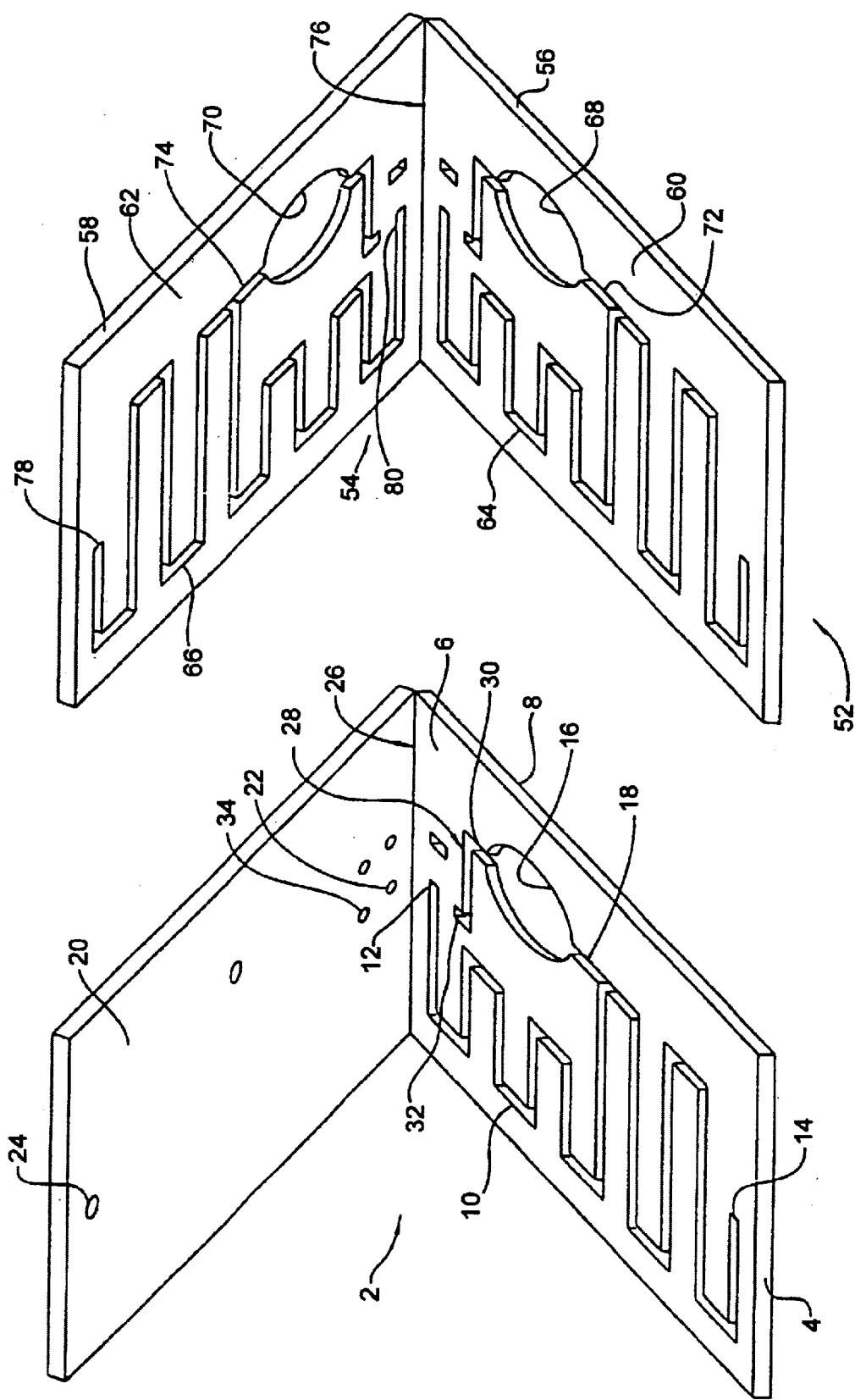

MICROANALYTICAL DEVICE AND USE THEREOF FOR CONDUCTING CHEMICAL PROCESSES

CROSS-REFERENCE TO RELATED APPLICATIONS

This application is a continuation-in-part of U.S. patent application Ser. No. 08/656,281, filed Apr. 27, 1998, now U.S. Pat. No. 6,033,628, which was a continuation-in part of U.S. patent application Ser. No. 08/482,245, filed Jun. 7, 1995, now U.S. Pat. No. 5,658,413, which was a continuation-in-part of U.S. patent application Ser. No. 08/326,111, filed Oct. 19, 1994, now U.S. Pat. No. 5,500,071, each of which is incorporated by reference herein.

TECHNICAL FIELD

This invention relates generally to the field of miniaturized devices for conducting chemical processes, and more particularly relates to novel microanalytical devices for conducting chemical processes such as separation (e.g., chromatographic, electrophoretic or electrochromatographic separation), screening and diagnostics (using, e.g., hybridization or other binding means), and chemical and biochemical synthesis (e.g., DNA amplification conducted using the polymerase chain reaction, or "PCR").

BACKGROUND

In sample analysis instrumentation, smaller dimensions generally result in improved performance characteristics and at the same time result in reduced production and analysis costs. Miniaturized separation systems, for example, provide more effective system design, result in lower overhead, and enable increased speed of analysis, decreased sample and solvent consumption and the possibility of increased detection efficiency.

Accordingly, several approaches have been developed in connection with miniaturization of devices for use in chemical analysis, particularly in micro-column liquid chromatography ($\mu$LC), wherein columns with diameters of 100 to 200 microns are used, in capillary electrophoresis (CE), wherein electrophoretic separation is conducted in capillaries on the order of 25 to 100 microns in diameter, and in microchannel electrophoresis (MCE), wherein electrophoresis is carried out within a microchannel on a substantially planar substrate. The conventional approach in miniaturization technology as applied to CE and $\mu$LC involves use of a silicon-containing material, i.e., a capillary fabricated from fused silica, quartz or glass. With MCE, an attractive method that is useful in conjunction with high throughput applications and enables reduction in overall system size relative to CE, miniaturized devices have been fabricated by silicon micromachining or lithographic techniques, e.g., microlithography, molding and etching. See, for example, Fan et al. (1994) *Anal. Chem.* 66(1):177–184; Manz et al., (1993) *Adv. in Chrom.* 33:1–66; Harrison et al. (1993), *Sens. Actuators*, B B10(2):107–116; Manz et at. (1991), *Trends Anal. Chem.* 10(5):144–149; and Manz et at. (1990) *Sensors and Actuators B (Chemical)* B1(1–6):249–255. The use of micromachining techniques to fabricate miniaturized separation systems in silicon provides the practical benefit of enabling mass production of such systems, and there are a number of techniques that have now been developed by the microelectronics industry for fabricating microstructures from silicon substrates. Examples of such micromachining techniques to produce miniaturized separation devices on silicon or borosilicate glass chips can be found in U.S. Pat. No. 5,194,133 to Clark et al., U.S. Pat No. 5,132,012 to Miura et al., U.S. Pat. No. 4,908,112 to Pace, and U.S. Pat. No. 4,891,120 to Sethi et al.

Use of silicon-containing substrates such as fused silica, quartz and glass in microanalytical devices is problematic in a number of ways. For example, silicon dioxide substrates have high energy surfaces and strongly adsorb many compounds, most notably bases. Silicon dioxide materials also dissolve to an appreciable extent when used with basic solutions. Furthermore, when used in electrophoretic applications, the internal surface of a silica capillary or microchannel will be negatively charged at basic pH as a result of deprotonation of surface silanol groups (i.e., they are in the form of anionic, Si—O$^-$, groups). The surface charge on the interior of the capillary or microchannel not only exacerbates the problem of unwanted adsorption of solute, but also modulates the velocity of electroosmotic flow (also termed "electroendoosmotic flow" or EOF) on an unmodified surface, in turn affecting the sensitivity and reproducibility of the chemical analysis conducted. (That is, the EOF velocity is a function of zeta potential $\zeta$, which is essentially determined by surface charge.) Microfabrication using silicon per se is similarly problematic insofar as a silica surface will form on a silicon substrate under even mildly oxidizing conditions.

For the foregoing reasons it would be desirable to fabricate microanalytical devices from materials that are not silicon-based, e.g., using inexpensive and readily available polymeric materials. It would also be desirable to extend the utility of microanalytical devices beyond electrophoretic and chromatographic separation techniques to other types of chemical processes, processes that may involve high temperatures, extremes of pH, harsh reagents, or the like. The present invention provides such microanalytical devices.

One area with which the present invention is particularly useful is in bioanalysis. An important technique currently used in bioanalysis and in the emerging field of genomics is the polymerase chain reaction (PCR) amplification of DNA. As a result of this powerful tool, it is possible to start with otherwise undetectable amounts of DNA and create ample amounts of the material for subsequent analysis. The technique is described in U.S. Pat. No. 4,683,195 to Mullis et al. and related U.S. Pat. Nos. 4,683,202, 4,800,159 and 4,965,188 to Mullis et al. Automated systems for performing PCR are known, as described, for example, in U.S. Pat. Nos. 5,333,675 and 5,656,493 to Mullis et al. PCR uses a repetitive series of steps to create copies of polynucleotide sequences located between two initiating ("primer") sequences. Starting with a template, two primer sequences (usually about 15–30 nucleotides in length), PCR buffer, free deoxynucloside tri-phosphates (dNTPs), and thermostable DNA polymerase (commonly Taq polymerase), one mixes these components, and then heats to separate the double-stranded DNA. A subsequent cooling step allows the primers to anneal to complementary sequences on single-stranded DNA molecules containing the sequence to be amplified. Replication of the target sequence is then accomplished by the DNA polymerase which produces a strand of DNA that is complementary to the template. Repetition of this process doubles the number of copies of the sequence of interest, and multiple cycles increase the number of copies exponentially.

Since PCR requires repeated cycling between higher and lower temperatures, PCR devices must be fabricated from materials capable of withstanding such temperature changes. The materials must be mechanically and chemically stable at high temperatures, and capable of withstanding repeated temperature changes without mechanical degradation. Furthermore, the materials must be compatible with the PCR reaction itself, and not inhibit the polymerase or bind DNA. To date, however, there remain many problems with performing PCR in microdevices. One problem involves the low thermal stability of many materials. That is, many types of materials, e.g., polymeric materials, cannot withstand the cycling temperatures used in PCR, typically in the range of about 37° C. to 90° C., without significant or complete loss of mechanical integrity. In addition, contaminants may be present on or leach out of a substrate surface, affecting the precise balance of appropriate ingredients (metal ions, salts, buffering systems, oligonucleotides, primers, and polymerases) required for PCR, in turn resulting in unsuccessful amplification reactions. Also, the polymerase enzyme or any of the components involved in the PCR reaction may bind to or become adsorbed on a microchannel surface. Contact between the polymerase and a substrate surface will generally result in irreversible denaturation. These types of "biofouling" are especially problematic with capillaries or microchannels of micron or submicron dimensions because of the very high surface area to volume ratio.

SUMMARY OF THE INVENTION

The present invention addresses the aforementioned needs in the art, and provides a novel microanalytical device in which chemical and biochemical reactions can be conducted. In its simplest embodiment, the microanalytical device comprises:

a substrate having first and second substantially planar opposing surfaces, with a cavity and at least one microchannel formed in the first planar surface, wherein the cavity serves as a reaction zone that is in fluid communication with each microchannel;

a cover plate arranged over the first planar surface, which in combination with the cavity defines a reaction chamber, and with each microchannel defining a microcolumn; and at least one inlet port and at least one outlet port communicating directly or indirectly with the reaction chamber, enabling the passage of fluid from an external source into and through the reaction chamber, wherein the substrate and the cover plate are comprised of a material that is thermally and chemically stable and resistant to biofouling. Preferred materials are those that exhibit reduced adsorption of solute, e.g., biomolecules such as proteins, nucleic acids, etc., and can be modified, coated or otherwise treated so as to optimize electroosmotic flow. In contrast to prior microanalytical systems, the present devices are useful in connection with a wide variety of processes, including not only electrophoretic, chromatographic and electrochromatographic separations, but also other chemical and biochemical processes that may involve high temperatures, extremes of pH, harsh reagents, or the like. Such processes include, but are not limited to, screening and diagnostics (using, e.g., hybridization or other binding means), and chemical and biochemical synthesis (e.g., DNA amplification, as may be conducted using PCR).

The invention is thus also addressed to a method for conducting a chemical or biochemical reaction using a small amount of fluid, wherein a microanalytical device as just described is provided, a reaction fluid is introduced into the reaction chamber through the inlet port, either directly or indirectly (i.e., the inlet port may be in direct communication with the reaction chamber or with an upstream microchannel feeding into the chamber), the desired reaction is conducted in the reaction chamber, and the product of the reaction is collected upon removal from the device through the outlet port. Microchannels present in fluid communication with the reaction chamber may be used to increase the concentration of a particular analyte or chemical component prior to processing in the reaction chamber, to remove potentially interfering sample or reaction components, to conduct preparative processing prior to chemical processing in the reaction chamber, and to isolate and purify the desire product.

BRIEF DESCRIPTION OF THE DRAWINGS

FIG. 4 is a perspective schematic view of a microanalytical device of the invention which includes both a separation microchannel and an on-device reservoir.

FIG. 5 is a plan view of a miniaturized column device having an on-device reservoir that is formed by the alignment of reservoir means formed on two opposing planar surfaces of a single flexible substrate.

DETAILED DESCRIPTION OF THE INVENTION

Figure 1:
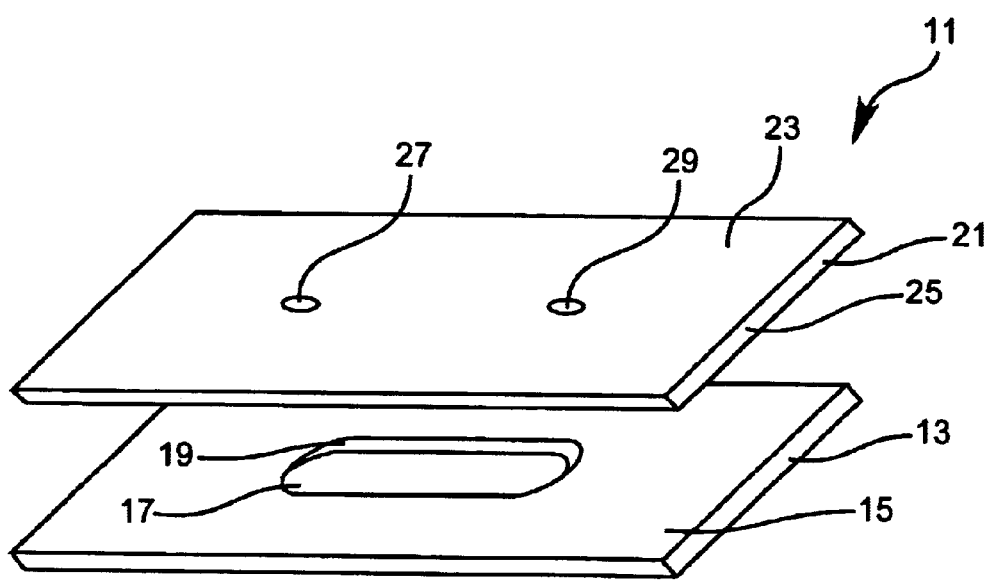
FIG. 1 is a perspective schematic view of one embodiment of a microanalytical device of the invention.

Before the invention is described in detail, it is to be understood that unless otherwise indicated this invention is not limited to particular materials, components or manufacturing processes, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a material" includes mixtures of materials, reference to "a reaction chamber" includes multiple reaction chambers, and the like.

In this specification and in the claims which follow, reference will be made to a number of terms which shall be defined to have the following meanings:

The term "microanalytical device" refers to a device having features of micron or submicron dimensions, and which can be used in any number of chemical processes involving very small amounts of fluid. Such processes include, but are not limited to, electrophoresis (e.g., CE or MCE), chromatography (e.g., $\mu$LC), screening and diagnostics (using, e.g., hybridization or other binding means), and chemical and biochemical synthesis (e.g., DNA amplification as may be conducted using the polymerase chain reaction, or "PCR"). The features of the microanalytical devices are adapted to the particular use. For example, microanalytical devices that are used in separation processes, e.g., MCE, contain microchannels (termed "microcolumns" herein when enclosed, i.e., when the cover plate is in place on the microchannel-containing substrate surface) on the order of 1 $\mu$m to 200 $\mu$m in diameter, typically 10 $\mu$m to 75 $\mu$m in diameter, and approximately 0.1 to 50 cm in length. Microanalytical devices that are used in chemical and biochemical synthesis, e.g., DNA amplification, will generally contain reaction zones (termed "reaction chambers" herein when enclosed, i.e., again, when the cover plate is in place on the microchannel-containing substrate surface) having a volume of about 1 $\mu$l to about 500 $\mu$l, typically about 10 $\mu$l to 200 $\mu$l.

As used herein, the term "detection means" refers to any means, structure or configuration which allows one to interrogate a sample within a microanalytical device of the invention using analytical detection techniques well known in the art. Thus, a detection means can comprise one or more openings that communicate with, for example, a reaction chamber or microchannel, and allow an external detection device to be interfaced with the chamber or microchannel to detect an analyte therein. By the arrangement of two detection means opposite each other relative to the reaction chamber or the like, a "detection path" is formed, allowing detection of analytes passing through the reaction chamber using detection techniques well known in the art. An "optical detection path" refers to a configuration or arrangement of detection means to form a path whereby electromagnetic radiation is able to travel from an external source to a means for receiving radiation, wherein the radiation traverses the reaction chamber, microchannel, or the like. In this configuration, analytes passing through the microanalytical device can be detected via transmission of radiation orthogonal to the direction of fluid flow. A variety of external optical detection techniques can be readily interfaced with the present microanalytical devices, including, but not limited to, UV/Vis, Near IR, fluorescence, refractive index (RI) and Raman techniques.

As used herein, a "transparent substance" refers to a substance capable of transmitting light of different wavelengths. Thus, a "transparent sheet" is defined as a sheet of a substance that is transmissive to specific types of radiation or particles of interest. Transparent sheets that may be employed in conjunction with the invention are formed from materials such as quartz, sapphire, diamond and fused silica, or from polymeric materials such as polystyrene and styrene-butadiene copolymer. "Optically transparent" refers to a material capable of transmitting light of wavelengths in the range of about 150 nm to 800 nm.

A "detection intersection" refers to a configuration wherein a plurality of detection means that communicate with the interior of the present microanalytical devices converge at a particular location therein. A number of detection techniques can be simultaneously performed on a sample or separated analyte at the detection intersection. A detection intersection is formed when a plurality of detection paths cross, or when a detection means such as an aperture communicates with the separation compartment at substantially the same point as a detection path. The sample, or a separated analyte, can thus be analyzed using a combination of UV/Vis and fluorescence techniques, optical and electrochemical techniques, optical and electrical techniques, or like combinations to provide highly sensitive detection information. See, e.g., Beckers et al. (1988) *J. Chromatogr.* 452:591–600; and U.S. Pat. No. 4,927,265, to Brownlee.

The term "liquid phase analysis" is used to refer to any analysis which is carried out on a solute in the liquid phase. Accordingly, "liquid phase analysis" as used herein includes chromatographic separations, electrophoretic separations, and electrochromatographic separations. The general term "analysis" refers to characterization of a sample or identification of one or more components therein, and is distinct from a chemical or biochemical "process" in which a material is chemically or biochemically altered to produce a desired product.

"Chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly, electrophoretic separations include separations performed in columns packed with gels (such as polyacrylamide, agarose and combinations thereof) as well as separations performed in solution.

"Electrochromatographic" separations refer to separations effected using a combination of electrophoretic and chromatographic techniques. Exemplary electrochromatographic separations include packed column separations using electromotive force (Knox et al. (1987) *Chromatographia* 24:135; Knox et al. (1989) *J. Liq. Chromatogr* 12:2435; Knox et al. (1991) *Chromatographia* 32:317), and micellar electrophoretic separations (Terabe et al. (1985) *Anal. Chem.* 57:834–841).

The term "injection molding" is used to refer to a process for molding plastic or nonplastic ceramic shapes by injecting a measured quantity of a molten plastic or ceramic substrate into dies (or molds). In one embodiment of the present invention, miniaturized devices can be produced using injection molding.

The term "embossing" is used to refer to a process for forming polymer, metal or ceramic shapes by bringing an embossing die into contact with a pre-existing blank of polymer, metal or ceramic. A controlled force is applied between the embossing die and the pre-existing blank of material such that the pattern and shape determined by the embossing die is pressed into the pre-existing blank of polymer, metal or ceramic. The term "hot embossing" is used to refer to a process for forming polymer, metal or ceramic shapes by bringing an embossing die into contact with a heated pre-existing blank of polymer, metal or ceramic. The pre-existing blank of material is heated such that it conforms to the embossing die as a controlled force is applied between the embossing die and the pre-existing blank. The resulting polymer, metal or ceramic shape is cooled and then removed from the embossing die.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated with high energy radiation using a synchrotron source to create desired microstructures (such as channels, ports, apertures, and micro-alignment means), thereby forming a primary template.

The term "motive force" is used to refer to any means for inducing movement of a sample along a column in a liquid phase analysis, and includes application of an electric potential across any portion of the column, application of a pressure differential across any portion of the column or any combination thereof.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

One embodiment of the present invention is represented in FIG. 1, which schematically illustrates a microanalytical device that can be used in conducting a chemical process such as PCR. The device is generally represented at 11, comprising substrate 13 having a substantially planar surface 15 containing a reaction zone 17 in the form of a shallow cavity, i.e., a cavity having a depth of micron or even submicron dimensions. A cover plate 21 is shown arranged over with substrate 13. Prior to use of the device, the underside 25 of the cover plate is aligned with and placed against the surface 15 of substrate 13. The cover plate, in combination with the reaction zone 17, forms a reaction chamber in which the desired chemical process is carried out. Fluid, e.g., sample to be analyzed, analytical reagents, reactants or the like, are introduced into the reaction chamber from an external source through inlet port 27; outlet port 29 enables passage of fluid from the reaction chamber to an external receptacle. Accordingly, "closure" of the device by aligning the cover with the substrate and forming a seal therebetween results in formation of a reaction chamber into which fluids may be introduced through inlet port 27 and removed through outlet port 29. Preferably, a liquid-tight seal is formed by using pressure sealing techniques, by using external means to urge the pieces together (such as clips, tension springs or associated clamping apparatus), or by using adhesives well known in the art of bonding polymers, ceramics and the like.

Figure 2:
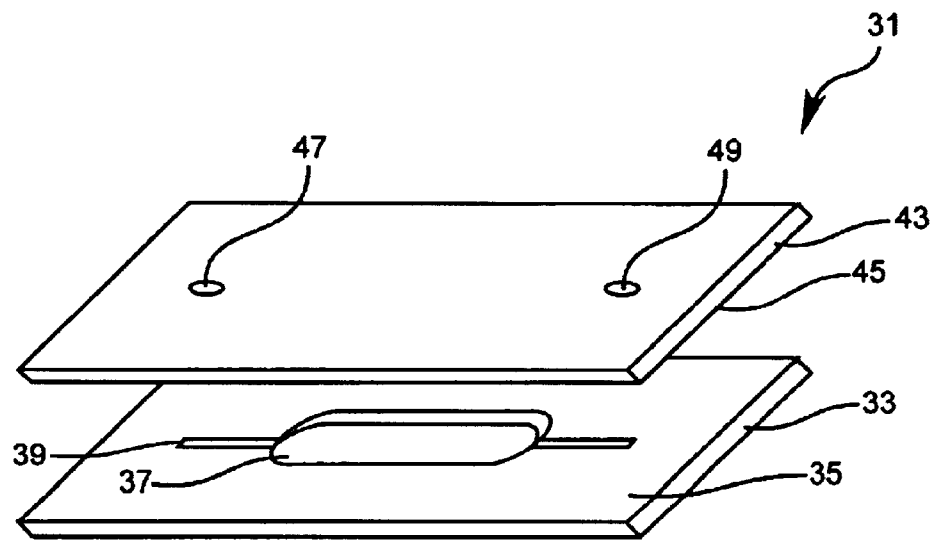
FIG. 2 is a perspective schematic view of a second embodiment of a microanalytical device of the invention.

In a related embodiment of the invention, as illustrated in FIG. 2, flow paths in the form of microchannels are incorporated into the substrate at either end of the reaction zone. That is, device 31 includes a substrate 33 having a substantially planar surface 35 containing a reaction zone 37, again in the form of a shallow cavity. An upstream microchannel 39 in the substrate surface is in fluid communication with the upstream region of reaction zone 37, while downstream microchannel 41 is in fluid communication with the downstream region of reaction zone 37. The cover plate 43 is shown arranged over substrate 33 with its underside 45 facing the substrate surface. The underside 45 of the cover plate is aligned with the substrate and placed against surface 35 prior to use of the device. Closure of the device in this manner, i.e., by aligning the cover with the substrate and forming a seal therebetween results in formation of a reaction chamber, an upstream microcolumn and a downstream microcolumn. Upon closure of the device, inlet port 47 in the cover plate allows introduction of fluid from an external source into the upstream microcolumn, while outlet port 49, also in the cover plate, allows removal of fluid from the downstream microcolumn. The upstream microcolumn may be used as a concentrating means to increase the concentration of a particular analyte or chemical component prior to chemical processing in the reaction chamber. Unwanted, potentially interfering sample or reaction components can also be removed using the upstream microcolumn in this way. In addition, or in the alternative, the upstream microchannel can serve as a microreactor for preparative chemical or biochemical processes prior to chemical processing in the reaction chamber. Such preparative processes can include labeling, protein digestion, and the like. The downstream microcolumn may be used as a purification means to remove unwanted components, unreacted materials, etc. from the reaction chamber following completion of chemical processing. This may be accomplished, for example, by packing the downstream microcolumn or coating its interior surface with a material that selectively removes certain types of components from a fluid or reaction mixture.

Figure 3:
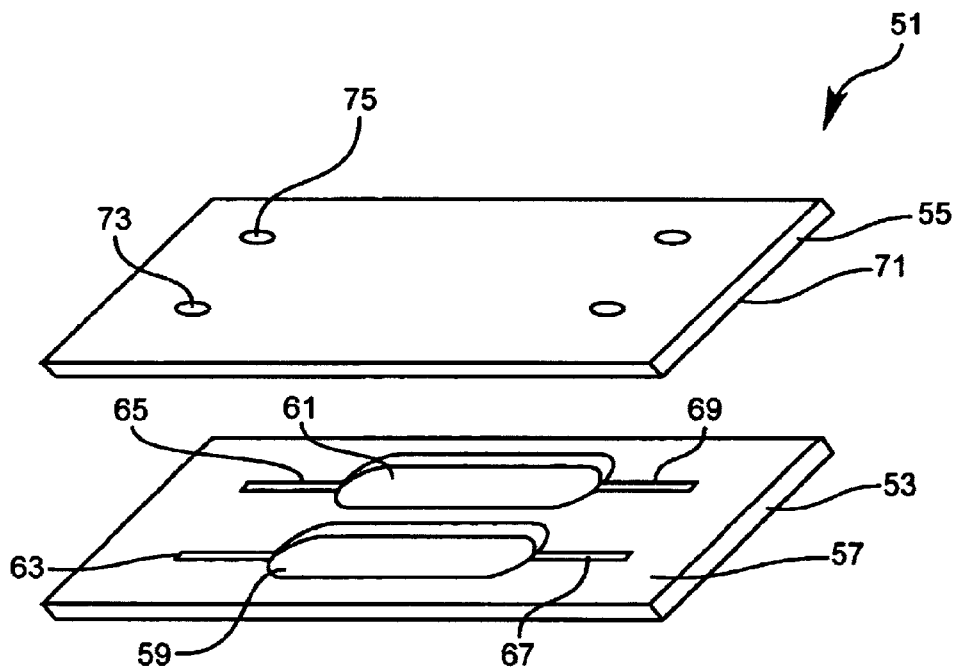
FIG. 3 is a perspective schematic view of another embodiment of a microanalytical device of the invention.

It will be appreciated that a device may be fabricated so as to contain two or more reaction zones and optional microchannels in fluid communication therewith. An example of such a device is illustrated in FIG. 3, shown generally at 51 as comprising substrate 53 and cover plate 55 aligned therewith. The upper surface 57 of the substrate, a substantially planar surface, is provided with a first reaction zone 59 and a second reaction zone 61. A first upstream microchannel 63 is in fluid communication with the upstream region of first reaction zone 59, and a second upstream microchannel 65 is in fluid communication with the upstream region of second reaction zone 61. Correspondingly, a first downstream microchannel 67 is in fluid communication with the downstream region of first reaction zone 59, and a second downstream microchannel 69 is in fluid communication with the downstream region of second reaction zone 61. Upon closure of the device by placement of the underside 71 of cover plate 55 against substrate surface 57, two reaction chambers are formed from the first and second reaction zones 59 and 61, along with two upstream microcolumns (formed from the first and second upstream microchannels 63 and 65) and two downstream microcolumns (formed from the first and second downstream microchannels 67 and 69). A first inlet port 73 in the cover plate 55 is aligned with the upstream terminus of first upstream microchannel 63, and a second inlet port 75 is aligned with the upstream terminus of second upstream microchannel, the first and second inlet ports 73 and 75 respectively providing for introduction of fluid from an external source into the first and second upstream microcolumns. Correspondingly, a first outlet port 77 in the cover plate 55 is aligned with the downstream terminus of the first downstream microchannel, and a second outlet port 79 is aligned with the downstream terminus of the second downstream microchannel, the first and second outlet ports 77 and 79 thereby providing for removal of fluid from the first and second downstream microcolumns, respectively. In this embodiment and in the embodiments of FIGS. 1 and 2, the substrate and cover plate may be joined at one edge, such that closure of the device is effected by folding the cover plate onto the substrate. The edge may include a fold means such as a row of spaced-apart perforations, depressions or apertures, having any shape, e.g., circular, diamond, hexagonal, etc., that promote folding and thus hinge formation.

The materials used to form the substrates and cover plates in the microanalytical devices of the invention are selected with regard to physical and chemical characteristics that are desirable for a particular application. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser etching, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. Also, all device materials used should be chemically inert and physically stable with respect to any reagents with which they comes into contact, under the reaction conditions used (e.g., with respect to pH, electric fields, etc.). For use in chemical processes involving high temperatures, e.g., PCR, it is important that all materials be chemically and physically stable within the range of temperatures used. For use with optical detection means, the materials used should be optically transparent, typically transparent to wavelengths in the range of about 150 nm to 800 nm. Silicon, silicon dioxide and other silicon-containing materials should be avoided, and preferred materials are those that do not strongly adsorb solutes, e.g., proteins or other biomolecules. Suitable materials for forming the present devices include, but are not limited to, polymeric materials, ceramics (including aluminum oxide and the like), glass, metals, composites, and laminates thereof.

Polymeric materials are particularly preferred herein, and will typically be organic polymers that are either homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Polyimide is of particular interest, and has proven to be a highly desirable substrate material in a number of contexts. It has been demonstrated, for example, that polyimides exhibit low sorptive properties towards proteins, which are known to be particularly difficult to analyze in prior silicon dioxide-based systems. Polyimides are commercially available, e.g., under the tradename Kapton®, (DuPont, Wilmington, Del.) and Upilex® (Ube Industries, Ltd., Japan).

The devices of the invention may also be fabricated from a "composite," i.e., a composition comprised of unlike materials. The composite may be a block composite, e.g., an A-B-A block composite, an A-B-C block composite, or the like alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, available from DuPont (Wilmington, Del.), that has been co-extruded with a second, thin layer of a thermal adhesive form of polyimide known as KJ®, also available from DuPont (Wilmington, Del.).

The surfaces of the substrates and cover plates may be chemically modified to provide desirable chemical or physical properties, e.g., to reduce adsorption of molecular moieties to the interior walls of a microchannel or reaction chamber, and to reduce EOF. For example, the surface of a polymeric or ceramic substrate may be coated with or functionalized to contain electrically neutral molecular species, zwitterrionic groups, hydrophilic or hydrophobic oligomers or polymers, etc. With polyimides, polyamides, and polyolefins having reactive sites or functional groups such as carboxyl, hydroxyl, amino and haloalkyl groups (e.g., polyvinyl alcohol, polyhydroxystyrene, polyacrylic acid, polyacrylonitrile, etc.), or with polymers that can be modified so as to contain such reactive sites or functional groups, it is possible to chemically bond groups to the surface that can provide a variety of desirable surface properties. An exemplary modified substrate is polyimide functionalized so as to contain surface-bound water-soluble polymers such as polyethylene oxide (PEO), which tends to reduce unwanted adsorption and minimize nonspecific binding in biochemical processes, e.g., in DNA amplification and other methodologies involving hybridization techniques. The substrate surface may also be advantageously modified using surfactants (e.g., polyethylene oxide triblock copolymers such as those available under the tradename "Pluronic," polyoxyethylene sorbitan, or "TWEEN"), natural polymers (e.g., bovine serum albumin or "BSA"), or other moieties that provide the desired surface characteristics, particularly in reducing the sorption of biomolecules such as proteins.

It should also be emphasized that different regions of a single substrate may have chemically different surfaces, e.g., the interior surface of a microchannel may comprise a first material, while the interior surface of a reaction chamber in fluid communication with that microchannel may comprise a second material. For example, the reaction chamber or chambers may have interior surfaces that are coated or functionalized, e.g., with PEO or the like, while the interior surfaces of microchannels associated with the reaction chamber(s) may not be coated or functionalized. Also, upstream and downstream microchannels may be fabricated so as to contain an ion exchange resin, a metal chelating compound, an affinity adsorbent material, or the like, i.e., materials selected to purify a fluid or sample by removing one or more components or types of components therefrom. In this way, different components and features present in the same substrate may be used to conduct different chemical or biochemical processes, or different steps within a single chemical or biochemical process.

Fabrication: The present microanalytical devices can be fabricated using any convenient method, including, but not limited to, micromolding and casting techniques, embossing methods, surface micro-machining and bulk-micromachining. The latter technique involves formation of microstructures by etching directly into a bulk material, typically using wet chemical etching or reactive ion etching ("RIE"). Surface micro-machining involves fabrication from films deposited on the surface of a substrate. An exemplary surface micro-machining process is known as "LIGA." See, for example, Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35–36; Ehrfeld et al. (1988), "1988 LIGA Process: Sensor Construction Techniques via x-Ray Lithography," *Tech. Digest from IEEE Solid-State Sensor and Actuator Workshop*, Hilton Head, S.C.; Guckel et al. (1991) *J. Micromech. Microeng.* 1: 135–138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—i.e., diameters—on the order of microns.

A preferred technique for preparing the present microanalytical devices is laser ablation. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation will typically involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) *Laser Focus Electro Optics*, at pp. 54–70, and in U.S. Pat. Nos. 5,291,226 and 5,305,015 to Schantz et al.

The fabrication technique that is used must provide for features of sufficiently high definition, i.e., microscale components, channels, chambers, etc., such that precise alignment—"microalignment"—of these features is possible. "Microalignment" refers to the precise and accurate alignment of laser-ablated features, including the alignment of complementary microchannels or microcompartments with each other, inlet and/or outlet ports with microcolumns or reaction chambers, detection means with microcolumns or separation compartments, detection means with other detection means, projections and mating depressions, grooves and mating ridges, and the like.

The substrate of each embodiment of the invention may also be fabricated from a unitary piece, or it may be fabricated from two planar segments, one of which serves as a base and does not contain features, apertures, or the like, and the other of which is placed on top of the base and has the desired features, apertures, or the like, ablated or otherwise formed all the way through the body of the segment. In this way, when the two planar segments are aligned and pressed together, a substrate equivalent to a monolithic substrate (e.g., as shown at element 13 of FIG. 1) is formed.

Another embodiment of the invention is directed to a microanalytical device as shown in FIG. 4 that includes both a miniaturized column for conducting separation processes, e.g., electrophoretic or chromatographic separations, as well as a reservoir compartment that serves as a reaction chamber for carrying out one or more chemical or biochemical reactions. The device is shown generally at 2, comprising a selected substrate 4 having first and second substantially planar opposing surfaces indicated at 6 and 8 respectively, and fabricated from a material other than silicon or silicon dioxide. Preferably, although not necessarily, the material is UV-absorbing and laser ablatable. The substrate 4 has a microchannel 10 laser ablated or otherwise formed in first planar surface 6. It will be readily appreciated that although the microchannel 10 has been represented in a generally extended form, microchannels formed in the practice of the invention can have a variety of configurations, such as in a straight, serpentine, spiral, or any tortuous path desired, and having any number of different cross-sectional shapes, i.e., having any of a wide variety of channel geometries including semi-circular, rectangular, rhomboid, and the like, and the channels can be formed in a wide range of aspect ratios. In addition, two or more microchannels may be present in a single substrate. As indicated in FIG. 4, the microchannel 10 has an upstream terminus indicated at 12, and a downstream terminus indicated at 14.

The first planar surface 6 further includes an on-device reservoir means 16, formed from a cavity that has been laser ablated or otherwise fabricated in the first planar surface 6. The cavity can be formed in any geometry and with any aspect ratio, limited only by the overall thickness of the substrate 4, to provide a reservoir means having a desired volume. The reservoir means can be used to provide a makeup flow fluid, a fluid regulation function, or reagents for enhancing detection or separation of liquid sample constituents. The reservoir means may also serve as a reaction zone in which chemical or biochemical processes are to be conducted. Such processes, as noted earlier herein, include, but are not limited to, separation (e.g., chromatographic, electrophoretic or electrochromatographic separation), screening and diagnostics (using, e.g., hybridization or other binding means), and chemical and biochemical synthesis (e.g., DNA amplification as may be carried out using PCR). The reservoir means 16 is in fluid communication with the microchannel 10 via a fluid conducting means 18, which is formed from a duct laser ablated or otherwise fabricated in the first planar surface 6.

A cover plate 20 is arranged over the first planar surface 6 and, in combination with microchannel 10, forms an elongate separation microcolumn. Further, the cover plate 20, in combination with the reservoir means 16, forms a reservoir compartment (or when the reservoir means serves as a reaction zone, a "reaction chamber" will be formed upon placement of the cover plate on the substrate), and, likewise, in combination with the fluid conducting means 18, forms a fluid conducting compartment that communicates the reservoir compartment with the separation microcolumn. The cover plate 20 can be fixably aligned over the first planar surface 6 to form a liquid-tight separation microcolumn by using pressure sealing techniques, by using external means to urge the pieces together (such as clips, tension springs or associated clamping apparatus), or by using adhesives well known in the art of bonding polymers, ceramics and the like.

In one particular device configuration, the cover plate 20 comprises a discrete component, having a substantially planar surface capable of interfacing closely with the first planar surface 6 of the substrate 4. However, in a preferred device, the substrate and the cover plate are formed in a single, flexible substrate. Referring to FIG. 4, the flexible substrate includes first and second portions, corresponding to the substrate 4 and the cover plate 20, wherein each portion has a substantially planar interior surface. The first and second portions are separated by at least one fold means, generally indicated at 26, such that the portions can be readily folded to overlie each other. The fold means 26 can comprise a row of spaced-apart perforations in the flexible substrate, a row of spaced-apart slot-like depressions or apertures extending only partway through the flexible substrate, or the like. The perforations or depressions can have circular, diamond, hexagonal or other shapes that promote hinge formation along a predetermined straight line.

The device 2 of FIG. 4 can be formed by laser ablating a microchannel 10, a reservoir means 16 and a fluid conducting means 18 in the substrate 4. A separation microcolumn, reservoir compartment and a fluid conducting compartment are then provided by folding the flexible substrate at the fold means 26 such that the cover plate portion 20 encloses the microchannel, reservoir and fluid conducting means.

In each of the above-described devices, the cover plate 20 can also include a variety of apertures or other features which have been laser ablated or otherwise fabricated therein. Particularly, a first aperture can be arranged to communicate with the separation compartment (formed by the combination of microchannel 10 and cover plate 20) adjacent the upstream terminus 12 of the microchannel 10 to provide an inlet port 22. The inlet port enables the passage of fluid from an external source into the separation compartment when the cover plate 20 is arranged over the first planar surface 6. A second aperture can likewise be arranged to communicate with the separation microcolumn adjacent the downstream terminus 14 of the microchannel 10 to form an outlet port 24, enabling passage of fluid from the separation compartment to an external receptacle. Accordingly, a flow path extends from an upstream end of the separation microcolumn and passing to a downstream end thereof, whereby liquid phase analysis of samples can be carried out by communicating fluids from an associated source (not shown) through the inlet port, passing the fluids through the separation microcolumn, and allowing the fluids to exit the separation compartment via the outlet port.

Various means for applying a motive force along the length of the separation microcolumn, such as a pressure differential or electric potential, can be readily interfaced to the column device via the inlet and outlet ports, in any of the foregoing devices. In electrophoresis, a voltage gradient will be applied across the flow path from the inlet port to the outlet port, causing components in the flowing fluid to migrate at different rates proportional to their charge and/or mass. As will be appreciated by those skilled in the art, any convenient means may be employed for applying a voltage gradient across the flow path.

In the particular device configuration of FIG. 4, the fluid conducting means 18 enables passage of fluid from the reservoir means 16 into the separation microcolumn at a position substantially midway between the upstream and downstream termini, 12 and 14, of the microchannel 10. It is noted that although the fluid conducting means 18 has been depicted in this manner, the fluid conducting means can be arranged to communicate with the separation compartment at any position between, or at, the upstream and downstream termini thereof.

By allowing fluid communication between the fluid conducting compartment and the separation microcolumn, a number of separation or detection enhancing operations may be conducted during the course of fluid flow. For example, the reservoir means 16 can be used to deliver a liquid reagent or dye, e.g., a fluorescent indicator, which is capable of reacting with the analyte, for example to enhance the detectability thereof.

The reservoir means 16 may be used to deliver reagents such as organic additives, surfactants, ionic agents, inorganic agents or the like, which can be added to the separation microcolumn through an initial mixing step. The chemical or biochemical process conducted in the reaction chamber may be done with a separation process (carried out, for example, in an upstream microchannel in fluid communication with the reaction chamber) or a purification process (carried out, for example, in a downstream microchannel in fluid communication with the reaction chamber), in which case a number of reagents that affect selectivity and resolution may be introduced, including buffers, agents impacting solution ionic strength, agents that alter dielectric constant or viscosity, and surfactants either above or below their critical micellar concentration (CMC). Surfactants below the CMC may associate with the interior surface of the separation microcolumn and hence change the selectivity of a liquid phase separation system. Micellar formation due to the use of surfactants above the CMC may serve as a pseudo packed-column phase in a mechanism of separation known as micellar electrokinetic capillary chromatography (MEKC). Suitable surfactants for MEKC include SDS and CTAB. Additionally, chiral selectors (e.g., cyclodextrins, crown ethers, or the like) can be used to affect enhanced separation of optically active species.

A number of buffer types may be delivered from the reservoir means 16, such as, but not limited to, common organic buffers (e.g., acetate or citrate buffers), inorganic buffers (e.g., phosphate or borate buffers), or Good's buffers (e.g., MES, ACES, MOPS, CAPS, HEPES, and the like). Agents impacting solution ionic strength, such as neutral salts (e.g., NaCl, KCl, or LiCl), can alternatively be delivered from the reservoir means. Agents can also be delivered from the reservoir to affect the dielectric constant of a solution in the separation compartment. Suitable agents include common organic solvents such as, but not limited to, MeOH, EtOH, $CH_3CN$ and isopropyl alcohol. Further, a number of agents can be delivered from the reservoir means 16 to alter the viscosity of the solution passing through the separation compartment, such as methyl cellulose, dextran, polyacrylamide, polyethylene glycol, or polyvinyl alcohol. Agents which can be used in this manner to alter surface wettability include neutral surfactants (TWEEN, BRIJ or alkyl glucosides), zwitterionic surfactants (e.g., CHAPS or CHAPSO), and charged surfactants (SDS or CTAB).

The reservoir means 16 may also be used to optimize an analysis by applying increased pressure to the separation microcolumn after a solute has begun to separate. Specifically, the reservoir means can be employed to deliver a known volume of buffer to the separation microcolumn at a point after a separation has begun, thereby increasing the pressure exerted on the liquid sample.

In any of the above devices, optional means may also be provided for introducing a fluid from an external source into the reservoir compartment. Referring still to the device of FIG. 4, a fluid conducting means 28, comprising a duct laser ablated or otherwise fabricated in substrate 4, is depicted as having a first end 30 in fluid communication with the reservoir means 16. The fluid conducting means 28 has a second end 32 in fluid communication with an orifice 34 formed in the cover plate 20. Orifice 34 can comprise, for example, an aperture that has been laser ablated or otherwise fabricated in cover plate 20. Alternatively, the orifice can be positioned in the cover plate to be in direct fluid communication with the reservoir compartment. However, in each of above-described configurations, the orifice 34 allows interfacing of an external fluid source with the reservoir compartment, whereby externally contained buffers, reagents or like fluids can be introduced into the reservoir compartment for subsequent passage into the separation compartment. The external fluid source can be interfaced with the orifice through associated mechanical valving to provide a divertable fluid connection. This feature allows a variety of injection methods or other fluid introduction means to be used in order to introduce reagents or sample into the reservoir compartment via the orifice 34, including pressure injection, hydrodynamic injection or electrokinetic injection. The external valving and injection means can communicate with the orifice by butt-coupling thereto; however, any other suitable method of connection known in the art can also be used herein.

Referring now to FIG. 5, a variation on the aforementioned microanalytical device is shown wherein the device is generally indicated at 52, comprising a support body 54 having first and second component halves indicated at 56 and 58 respectively. The first and second component halves, 56 and 58, each have substantially planar interior surfaces, indicated at 60 and 62 respectively, wherein high definition features can be laser ablated or otherwise fabricated. More particularly, a first microchannel pattern 64 is laser ablated or otherwise fabricated in the first planar interior surface 60 and a second microchannel pattern 66 is laser ablated or otherwise fabricated in the second planar interior surface 62. The first and second microchannel patterns in the support body 54 provide the mirror image of each other. In like manner, the column device 52 includes first and second reservoir means, 68 and 70, formed from cavities laser ablated or otherwise fabricated in the first and second planar surfaces 60 and 62, respectively, wherein the cavities provide the mirror image of each other. First and second fluid conducting means, indicated at 72 and 74, are formed from ducts laser ablated or otherwise fabricated in the first and second planar surfaces, wherein the ducts are substantially the mirror image of each other. As described above, the fluid conducting means enables fluid communication between the reservoir means and the microchannels.

The column device 52 is assembled by aligning (such as by folding) the first and second component halves 56 and 58 in facing abutment with each other. The first and second component halves are held in fixable alignment with each other to form liquid-tight separation microcolumns, reservoir compartments and fluid conducting compartments using pressure sealing techniques, such as the application of tensioned force, or by use of adhesives well known in the art of liquid phase separation devices. As described above, the first and second component halves 56 and 58 are separated by at least one fold means, generally indicated at 76, such that the halves can be folded to overlie each other. In particularly preferred devices, the fold means 76 comprises a row of spaced-apart perforations in the substrate or spaced-apart slot-like depressions or apertures extending only partway through the substrate.

The device 52 further includes means for communicating associated external fluid containment means (not shown) with the separation microcolumn (formed by the alignment of microchannels 64 and 66) to provide a liquid-phase separation device. More particularly, a plurality of apertures can be laser ablated or otherwise fabricated in the support body 54, wherein the apertures extend from at least one exterior surface of the support body and communicate with at least one microchannel, said apertures permitting the passage of fluid therethrough. More particularly, an inlet port can be laser ablated or otherwise fabricated in the second component half 58 to communicate with a first end 78 of the microchannel 66. In the same manner, an outlet port can be laser ablated or otherwise fabricated in the second component half to communicate with a second end 80 of the microchannel 66.

Accordingly, a flow path extends from the first end 78 of the microchannel 66 to the second end 80 thereof. The flow path is established by communicating fluids from an associated source (not shown) through the inlet port, passing the fluids through the separation compartment formed by the alignment of microchannels 64 and 66, and allowing the fluids to exit the separation microcolumn via the outlet port.

Figure 6:
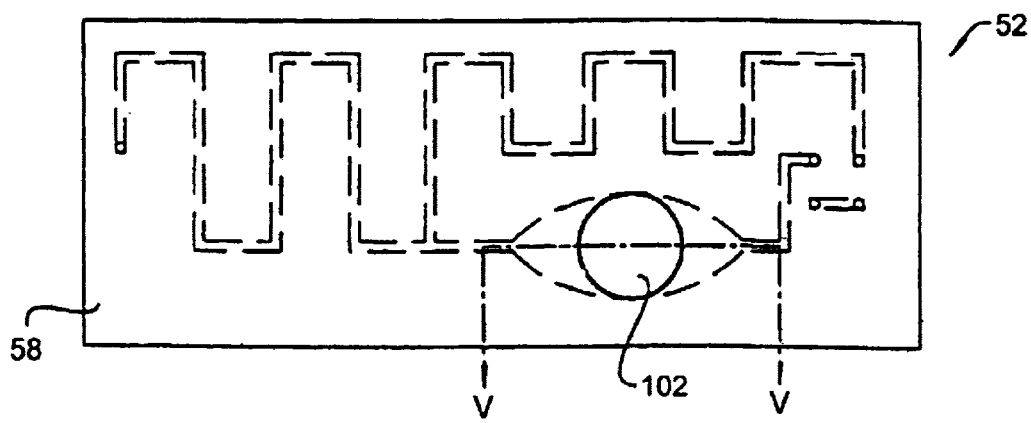
FIG. 6 is a plan view of exterior surface of a miniaturized column device having an optional actuator means disposed over an on-device reservoir compartment.
Figure 7:
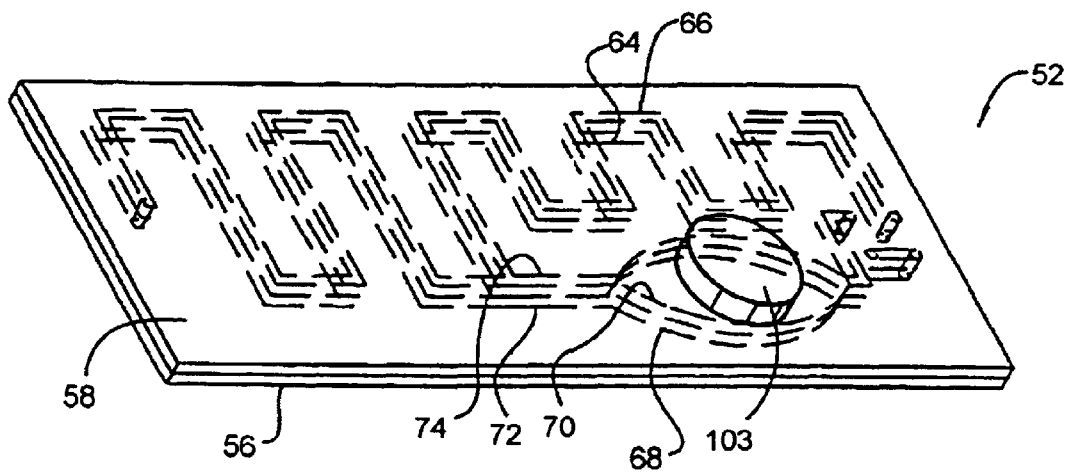
FIG. 7 is a pictorial representation of the miniaturized column device of FIG. 6.
Figure 8:
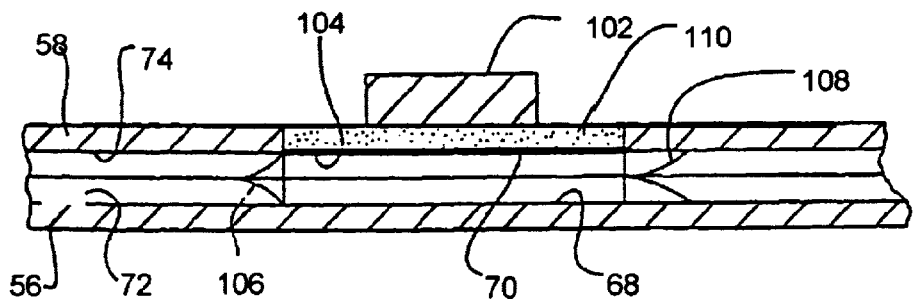
FIG. 8 is a cross-sectional view of the actuator of FIG. 6 taken along lines V—V and showing an optional membrane interposed between the reservoir and actuator means.

Optionally, the fluid may be displaced from the reservoir compartment by a motive means such as an actuator or the like. Referring to FIGS. 6–8, the microanalytical device 52 is depicted as including an optional actuator means 102 disposed over the reservoir compartment formed by the alignment of the first and second reservoir means 68 and 70. As best seen in the cross-sectional representation of FIG. 8, the reservoir compartment is optionally covered with thin membrane 104 to form a diaphragm-type pump. A first passive one-way microvalve 106 is optionally integrated into the fluid conducting compartment formed from the alignment of the first and second fluid conducting means 72 and 74 to prevent backflow of displaced fluid into the reservoir compartment, and a second passive one-way microvalve 108 is optionally integrated into reservoir filling means to ensure that the fluid being displaced from the reservoir compartment will travel toward the separation microcolumn.

Referring still to FIG. 8, an optional gas- or liquid-filled cavity 110 is disposed immediately above the membrane 104. The actuator means 102 can be employed to effect fluid displacement from the reservoir compartment by deflection of the membrane 104. Specifically, the actuator means 102 may act to directly deflect the membrane 104. Accordingly, the actuator means may be a piezoelectric, piston, solenoid or other type of membrane-deflecting device. Alternatively, the actuator means can be a heating means by which the temperature inside cavity 110 is regulated. The heating means can be a resistance-type heating means or any type of suitable heating means known in the art. Upon actuation, the temperature of the heating means increases, thereby heating the contents of cavity 110 and increasing the volume thereof, producing a downward deflection of membrane 104, and displacing fluid from the reservoir compartment, into the fluid conducting means past the valve 106, and into the separation microcolumn.

Alternatively, heating means 102 may be in thermal contact with the reservoir compartment itself. In this configuration, as the heating means temperature increases, the volume of the fluid in the reservoir compartment increases and is thereby displaced from the reservoir compartment into the separation microcolumn.

Other examples of pumping mechanisms which may be incorporated into the present devices include those which operate on the principles of ultrasonic-induced transport (Moroney et al. (1991) *Proc MEM S*'91, p. 277) or electrohydrodynamic-induced transport (Richter et al. (1991) *Proc MEM S*'91 p. 271). In addition, chemical valves composed of electrically driven polyelectrolyte gels (Osada (1991) *Adv. Materials* 3:107; Osada et al. (1992) *Nature* 355:242) may be used.

The use of transparent materials in the present microanalytical devices, i.e., for the substrate and preferably the cover plate, enables use of refractive-index (RI) detection to detect separated analytes of interest passing through the separation microcolumns. For example, an associated laser diode that emits radiation at a wavelength where the device material is "transparent" allows for a detection setup where no additional features need to be provided in the devices.

Optional detection means can be included in any of the present microanalytical devices. Referring particularly to the device of FIG. 3, one or more detection means can be laser ablated or otherwise fabricated in substrate 4 and/or cover plate 20. Preferably, the detection means will be disposed substantially downstream of the upstream terminus 12 of microcolumn 10, to enable detection of one or more components contained therein. For example, an aperture can be provided through substrate 4 to communicate with the separation channel 10. A corresponding aperture can likewise be formed in cover plate 20, and arranged so that it will be in coaxial alignment with the detection aperture in the substrate when the cover plate is affixed to the substrate. In a separation process, electrodes can be connected to the miniaturized column device via the subject corresponding apertures to detect separated analytes of interest passing through the separation compartment by electrochemical detection techniques. In one particular device configuration, the coaxially aligned apertures form an optical detection path, enabling the optical detection of separated analytes passing through the separation microcolumn via transmission of radiation orthogonal to the major axis of the separation microcolumn (and, accordingly, orthogonal to the direction of electroosmotic flow in an electrophoretic separation).

A wide variety of associated optical detection devices can be interfaced with the miniaturized columns using the optional detection means. Thus, detection of analytes in samples passing through the separation compartment can be readily carried out using UV/Vis, fluorescence, refractive index (RI), Raman and like spectrophotometric techniques.

Further, as will be readily appreciated, the use of optical detection means comprising apertures ablated into (or otherwise fabricated in) the substrate and cover plate provides great control over the effective optical detection pathlength. The resulting detection pathlength will be substantially equal to the combined thickness of the substrate 4 and the cover plate 20.

Figure 9:
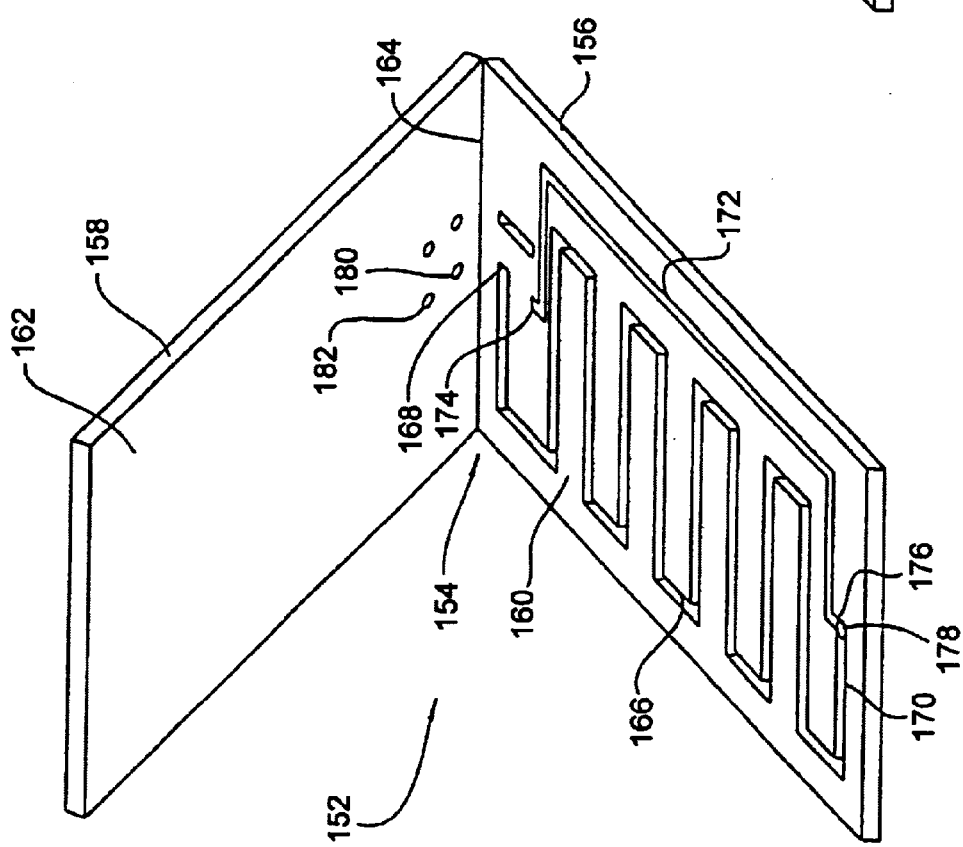
FIG. 9 is a plan view of a miniaturized column device which includes an on-device makeup flow compartment formed in the same planar surface as a separation compartment.

Microanalytical devices are also provided having a makeup flow means capable of supplying a makeup fluid stream to a downstream position on the separation microcolumn to enhance sample collection therefrom. Referring to FIG. 9, such a microanalytical device is generally indicated at 152, formed in a single substrate 154 having first and second portions 156 and 158, respectively. The first and second portions have substantially planar interior surfaces, 160 and 162, and are separated by at least one fold means, generally indicated at 164, which enables the portions to be folded to overlie each other as described above. The device 152 is formed by laser ablating or otherwise fabricating a separation microchannel 166 in the planar surface 160 of the first substrate portion 156. The microchannel extends between an upstream terminus 168 and a downstream terminus 170. A makeup channel 172, comprising a substantially elongate channel having an upstream terminus 174 and a downstream terminus 176 is likewise laser ablated or otherwise fabricated in the planar surface 160, wherein the makeup channel extends substantially along the length of the separation microchannel. The downstream terminus 176 of the makeup channel 172 is arranged to communicate with the downstream terminus 170 of the separation microchannel 166. More particularly, the downstream termini of the separation microchannel and the makeup channel converge at an outlet aperture 178 that has been laser ablated or otherwise fabricated in the first substrate portion 156.

A separation microcolumn and a makeup flow compartment are formed when the flexible substrate 154 is folded about the fold means 164 such that the substantially planar interior surface 162 of the second substrate portion 158 overlies the first substrate portion 156. A separation compartment inlet 180 is provided, comprising an aperture laser ablated or otherwise fabricated in the second substrate portion 158 and arranged to cooperate with the upstream terminus 168 of the separation microcolumn when the interior surfaces of the substrate portions are aligned with each other as described above. Thus, a flow path extending from the upstream terminus of the separation microcolumn and passing to the downstream terminus is provided, whereby liquid phase analysis of samples can be carried out by communicating fluids from an associated source (not shown) through the inlet 180, passing the fluids through the separation microcolumn, and allowing the fluids to exit the separation microcolumn via the outlet aperture 178.

A makeup compartment inlet 182 is also provided, comprising an aperture in the second substrate portion 158 and arranged to cooperate with the upstream terminus 174 of the makeup channel when the interior surfaces of the substrate portions are aligned with each other. Thus, a makeup fluid stream can be passaged from the inlet 182 to converge with an eluate exiting from the separation microchannel at the outlet aperture 178.

Figure 10:
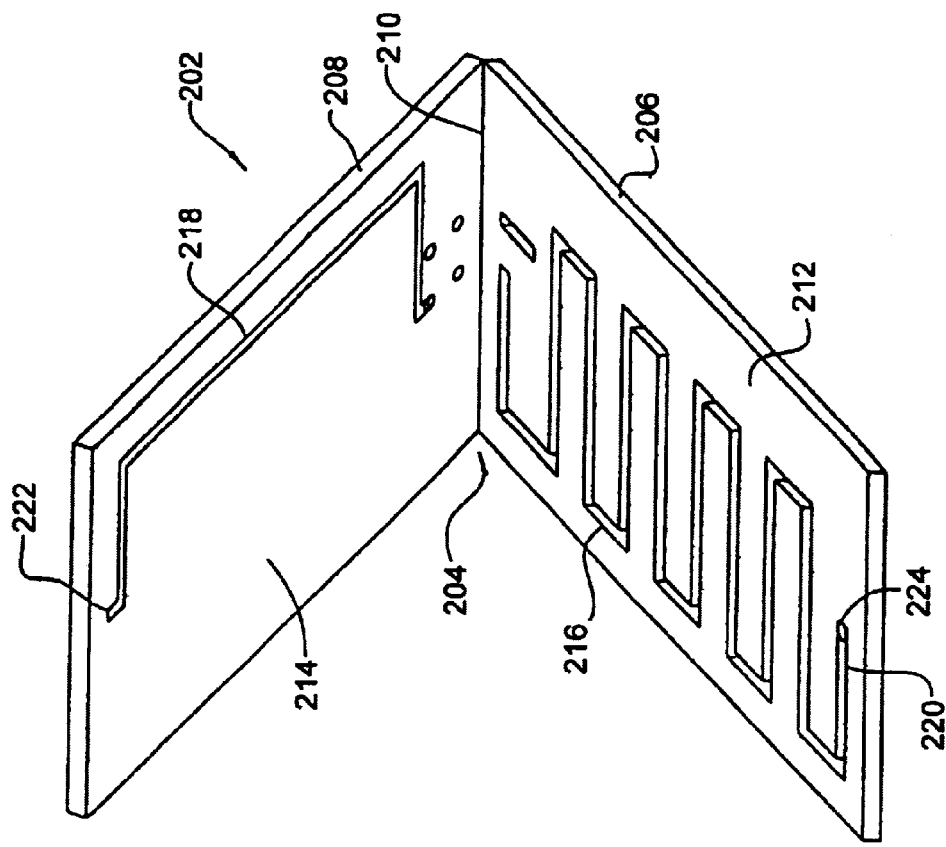
FIG. 10 is a plan view of a miniaturized column device having an on-device makeup flow compartment formed on a different planar surface than a separation compartment.

Referring now to FIG. 10, a related microanalytical device is generally indicated at 202. The subject device is formed from a single, preferably flexible substrate 204 having first and second portions, 206 and 208, wherein the portions are divided by fold means 210. The first and second substrate portions have substantially planar interior surfaces, 212 and 214. A separation microchannel 216 is laser ablated or otherwise fabricated in the first planar surface 212 and a makeup channel 218 is laser ablated or otherwise fabricated in the second planar surface 214. A separation microcolumn is formed when the substrate 204 is folded about fold means 210 such that the planar surface 214 overlies the separation microchannel 216. A makeup flow compartment is also formed when the substrate 204 is folded. A downstream terminus 220 of the separation microchannel 216 and a downstream terminus 222 of the makeup channel 218 are arranged to converge at an outlet port 224, comprising a laser ablated or otherwise fabricated aperture formed in the substrate portion 206.

A number of optional detection means can be included in the above devices. Referring particularly to the device depicted in FIG. 9, one or more detection means, such as corresponding apertures, can be ablated or otherwise formed in each portion of the substrate 154 as has been described. Preferably, the detection means will be disposed substantially downstream of the upstream terminus 168 of the separation microchannel 166 to enable detection of components passing through the separation microchannel.

Figure 11:
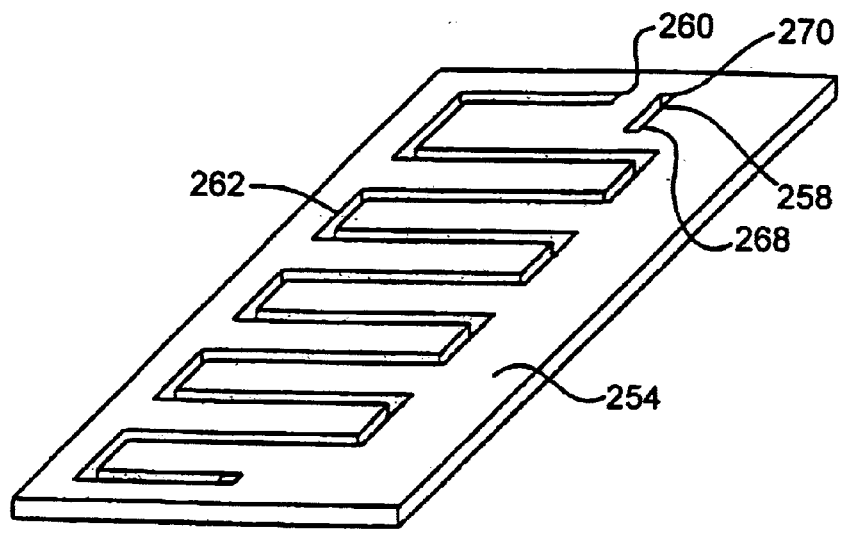
FIG. 11 is a plan view of a miniaturized column device having an optional sample introduction means ablated or otherwise formed in a planar substrate.
Figure 12:
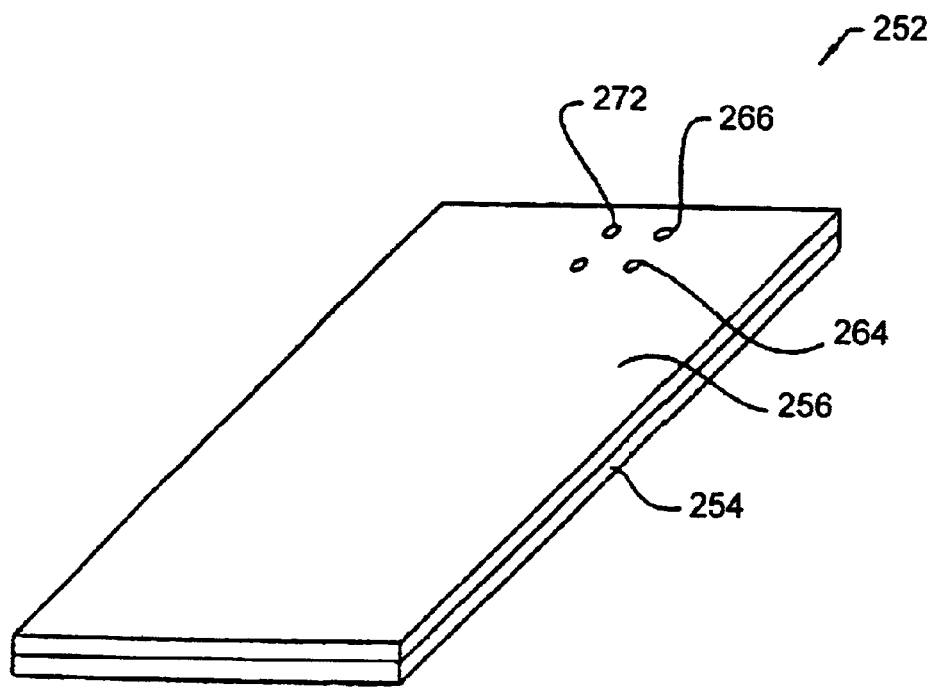
FIG. 12 is a plan view of the miniaturized column device of FIG. 11 having a cover plate aligned over the planar substrate.

Referring now to FIGS. 11 and 12, the above-described microanalytical devices can include an optional fluid introduction means. Particularly, a device 252 is provided having fluid introduction means laser ablated or otherwise fabricated in both a substrate 254 and a cover plate 256. As best seen in FIG. 11, a by-pass channel 258 is present in substrate 254, such that the channel 258 is disposed near an upstream terminus 260 of a separation microcolumn 262. Two apertures 264 and 266 are present in the cover plate 256 and positioned to cooperate with first and second ends (indicated at 268 and 270, respectively) of the by-pass channel 258 when the cover plate is arranged over the substrate. A volumetric compartment is formed by aligning the cover plate 256 over the substrate 254 to enclose the by-pass channel 258, whereby a fluid being held in an external reservoir can be introduced into the volumetric compartment to form a plug of a known volume (defined by the dimensions of the volumetric compartment). The plug can be delivered to the upstream terminus 260 of the separation microcolumn 262 via an inlet port 272, comprising an aperture in the cover plate 256. Delivery of the plug can be carried out by communicating external mechanical valving with the inlet port and apertures 264 and 266, and flushing solution through the volumetric compartment into the separation microcolumn.

The by-pass channel 258 and apertures 264 and 266 enable a wide variety of fluid introduction techniques to be practiced with the present devices. Further, having a by-pass channel that is not connected to the separation microcolumn allows a user to flush a sample or the like through the by-pass channel without experiencing sample carry-over or column contamination.

In another embodiment of the invention, a liquid phase separation apparatus is provided, wherein the apparatus is formed from the operative combination of any microanalytical device as described above and a variety of peripheral elements that enable liquid phase separations to be carried out within the column devices.

Figure 13:
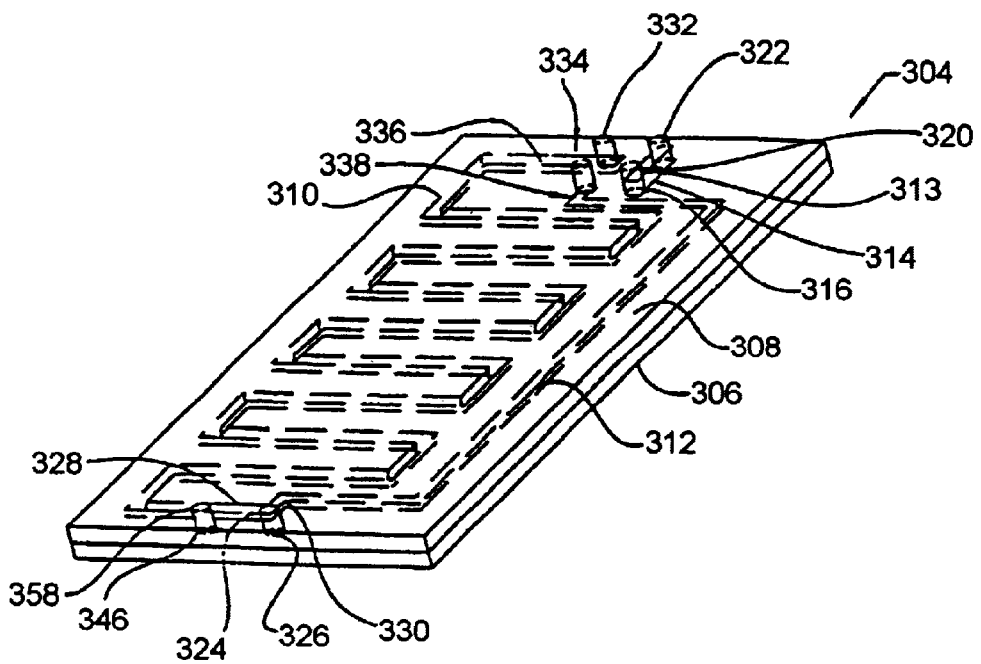
FIG. 13 is a pictorial representation of a miniaturized planar column device and depicts a preferred configuration of a coplanar separation and makeup flow compartments.
Figure 14:
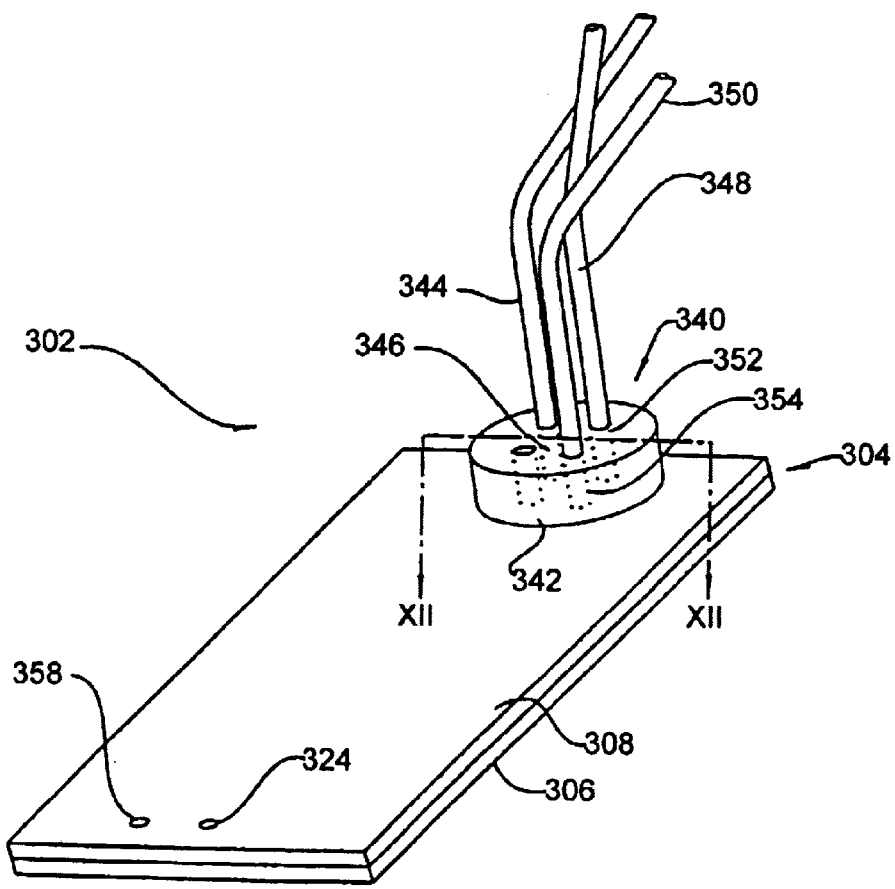
FIG. 14 is a pictorial representation of a liquid phase separation apparatus that includes the device of FIG. 11 and an externally arranged injection means interfaced with the column device.

Referring to FIGS. 13 and 14, a liquid phase separation apparatus is generally indicated at 302. The apparatus includes a miniaturized column 304, having a substrate portion 306 and a cover plate portion 308. A separation microchannel 310 and an optional makeup flow channel 312 are laser ablated or otherwise fabricated in the substrate 306 and, in combination with the cover plate 308, form a separation microcolumn and a makeup flow compartment.

An aperture 324 is arranged in the cover plate 308 to correspond with an outlet port 326. The outlet port comprises an aperture, laser ablated or otherwise fabricated in the substrate 306, and arranged such that the aperture 324 and the outlet port are positioned in coaxial alignment with each other when the cover plate is fixably aligned over the substrate. The outlet port 326 is also in fluid communication with the downstream terminus 328 of separation microchannel 310 and the downstream terminus 330 of makeup flow channel 312. An inlet port 332, comprising an aperture laser ablated or otherwise fabricated in the cover plate 308, is arranged to communicate with the upstream terminus 334 of the separation microchannel 310, and allows the formation of a flow path, extending from the upstream terminus 334 of the separation microchannel to the downstream terminus 328, and exiting through the outlet port 326.

A makeup fluid inlet 336, comprising an aperture laser ablated or otherwise fabricated in the cover plate 308, is arranged to be in fluid communication with the upstream terminus 338 of the makeup flow channel 312 and allows the formation of a makeup fluid flow path extending from the upstream terminus 338 of the makeup flow channel to the downstream terminus 330, and exiting through the outlet port 326.

Figure 15:
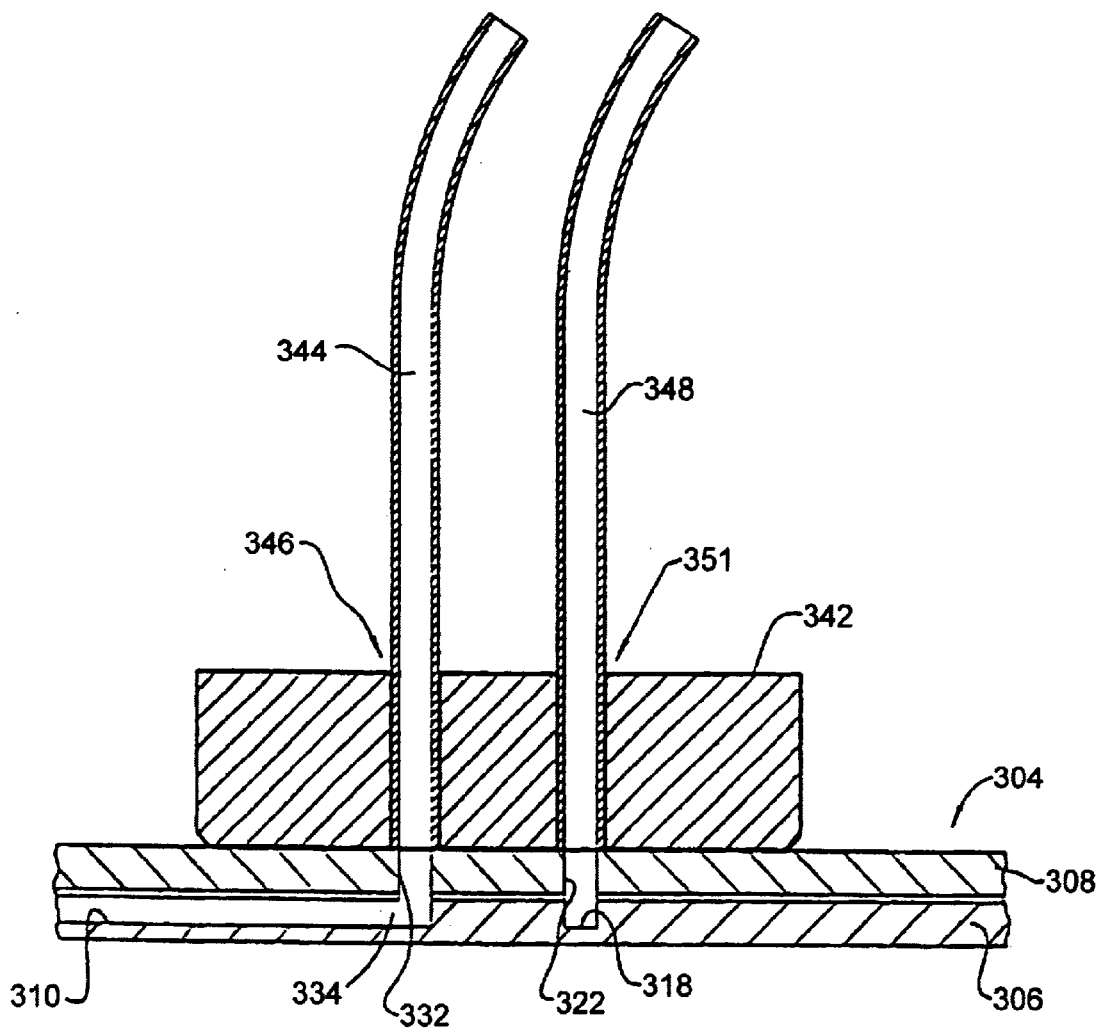
FIG. 15 is a cross-sectional view of the injection means of FIG. 14 taken along lines XII—XII.
Figure 16:
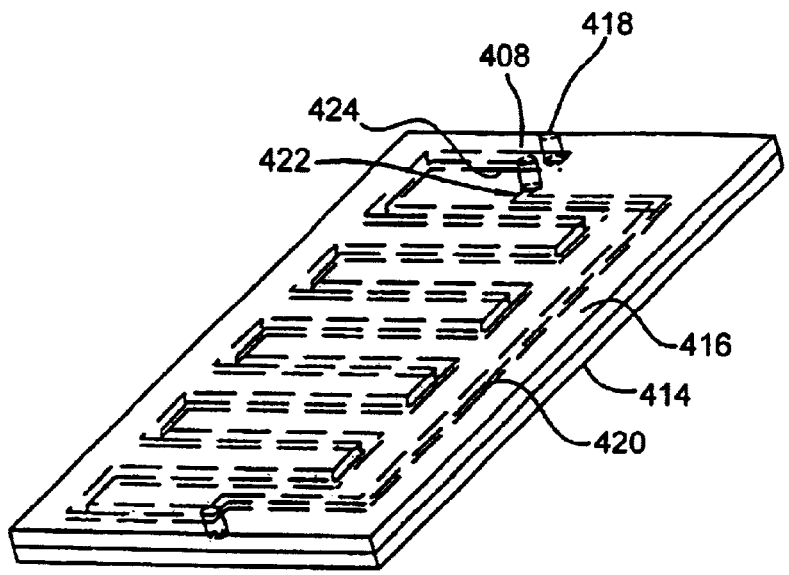
FIG. 16 is a pictorial representation of a miniaturized planar column device similar to the device of FIG. 13.

Referring now to FIGS. 14 and 15, the apparatus 302 further includes an injection means, generally indicated at 340, which allows for the distribution of externally housed liquid samples, buffers, reagents, and makeup flow fluids into the separation microcolumn and/or the makeup flow compartment. Thus, in one configuration, the sample introduction means can comprise a manifold 342 that closely engages the cover plate 308 of the miniaturized column device 304, and enables the interface of associated conduits and fluid containment means with the inlet port 332 and/or the makeup fluid inlet 336.

The manifold 342 can be coupled to the cover plate 308 to form a liquid-tight interface using pressure sealing techniques known in the art. The manifold and cover plate can be mechanically urged together using clips, tension springs or any suitable clamping means known in the art. The manifold 342 generally includes a plurality of ports that are configured to correspond with the pattern of apertures and inlets present in the cover plate 308. Referring particularly to FIG. 15, a first conduit 344 can be used to interface an associated containment means (not shown) housing a sample or mixture to be separated, or a suitable buffer, with the separation microchannel 310. The conduit 344 is interposed within a port 346 in the manifold 342, and arranged to be in fluid communication with the upstream terminus 334 of the separation microchannel 310 via the inlet port 332. In this manner, fluids from the associated containment means can be readily delivered to the separation microcolumn using known injection methods.

The liquid phase separation apparatus 302 can include a column 304 having an optional bypass microchannel 314 laser ablated or otherwise fabricated in the substrate 306, whereby a volumetric compartment is formed in combination with the cover plate 308. The bypass microchannel has first and second termini, 316 and 318, which respectively cooperate with first and second laser ablated or otherwise fabricated apertures 320 and 322 that are arranged in the cover plate 308 to correspond with the subject termini when the cover plate is aligned over the substrate 306.

Second and third conduit means, 348 and 350, are respectively interposed within ports 352 and 354 in the manifold 342, whereby the conduit means communicate with the bypass microchannel 314 at the first and second termini, 316 and 318, via the first and second laser ablated or otherwise fabricated apertures 320 and 322. A plug having the dimensions of the volumetric compartment is thus provided by passing sample through the compartment from an associated containment means using the conduits 348 and 350 to provide a sample flow path to and from the containment means. By manually removing conduits 344, 348 and 350 from the manifold 342, and coupling manifold ports 352 and 346 together by way of a single conduit, a new flow path is provided that passes from the volumetric compartment to the upstream terminus 334 of the separation microcolumn. By coupling the manifold port 354 to a further conduit means that is in fluid communication with a second associated containment means housing a suitable liquid medium, the plug can be flushed from the volumetric compartment and delivered into the separation microcolumn by conveying medium from the second containment means to the manifold using known fluid injection methods.

Once the sample has been delivered to the separation microcolumn, various means for applying a motive force along the length of the separation microcolumn can be interfaced to the column device 404 using the manifold 406. For example, a pressure differential or electric potential can be established along the length of the separation microcolumn by coupling an external motive means to the upstream terminus of the separation microchannel via a manifold port.

The liquid phase separation apparatus 302 may further include detection means, disposed in the cover plate 308 and/or the substrate portion 306. The detection means can comprise one or more apertures or features that have been laser ablated or otherwise fabricated in the cover plate or substrate portion and communicate with the separation microcolumn at a position adjacent to, or substantially nearby, the downstream terminus 330 of the separation microchannel 310 to enable the detection of separated sample analytes or fluid components. Referring to FIGS. 13 and 14, one particular apparatus includes an aperture 356 in the substrate portion 306 which communicates with the separation microchannel 310 near the downstream terminus 330 thereof. A second aperture 358 is in the cover plate 308, and is arranged to be in coaxial alignment with the aperture 356 when the cover plate is aligned over the substrate as has been described above. The coaxial apertures allow electrodes to be connected to the miniaturized column device 304 via the subject corresponding apertures to detect separated analytes of interest passing through the separation microcolumn by electrochemical detection techniques. In one particular apparatus, the coaxially aligned apertures form an optical detection path, enabling the optical detection of separated analytes passing through the separation microcolumn. As will be appreciated by those skilled in the art, a wide variety of associated optical detection devices can be interfaced with the separation microcolumn via the coaxial apertures, enabling the practice of spectrophotometric techniques such as UV/Vis, fluorescence, refractive index (RI), Raman and the like to detect separated analytes or fluid components.

A liquid phase separation apparatus can also be designed to have a manifold means that is movable between a plurality of positions. Referring now to FIGS. 16, 17 and 18A–C, an apparatus 402 is depicted which includes a microanalytical device 404 as described herein, and a movable manifold means 406 detachably coupled to the column device 404 and arranged near the upstream terminus 408 of a separation microchannel 410 that has been laser ablated or otherwise fabricated in a planar surface 412 of the column substrate 414. A cover plate 416 is arranged over the planar surface 412 of the column substrate, and, in combination with the separation microchannel 410, forms a separation microcolumn. An inlet port 418, formed from an aperture laser ablated or otherwise fabricated in the cover plate 416, communicates with the upstream terminus 408 of the separation microchannel when the cover plate is positioned over the column substrate.

The device 404 also includes a makeup flow channel 420 laser ablated or otherwise fabricated in the planar surface 412. A makeup flow compartment is formed by the combination of the cover plate 416 and the makeup flow microchannel 420. The makeup flow channel has an upstream terminus, 422, which is in fluid communication with a makeup inlet port 424, comprising an aperture laser ablated or otherwise fabricated in the cover plate 416 and arranged to communicate with the terminus when the cover plate is positioned over the column substrate.

The manifold 406 includes a plurality of ports that are configured to correspond with various apertures and inlets present in the cover plate 416 when the manifold is moved between positions relative to the column device 404. In one particular apparatus, the movable manifold 406 comprises a rotor that is butt-coupled to a stator (not shown) present on the external surface of the miniaturized column device 404, whereby the rotor is capable of moving about the stator between selected positions relative to the column device. When the column device is formed in a polyimide substrate, a ceramic rotor, pressed to the device using tensioned force (to form a liquid-tight seal), is capable of rotating between selected aperture positions on the device due to the friction characteristics of the two materials. Other suitable rotors can be formed in rigid materials such as glass and other non-conductive substrates.

Figure 17:
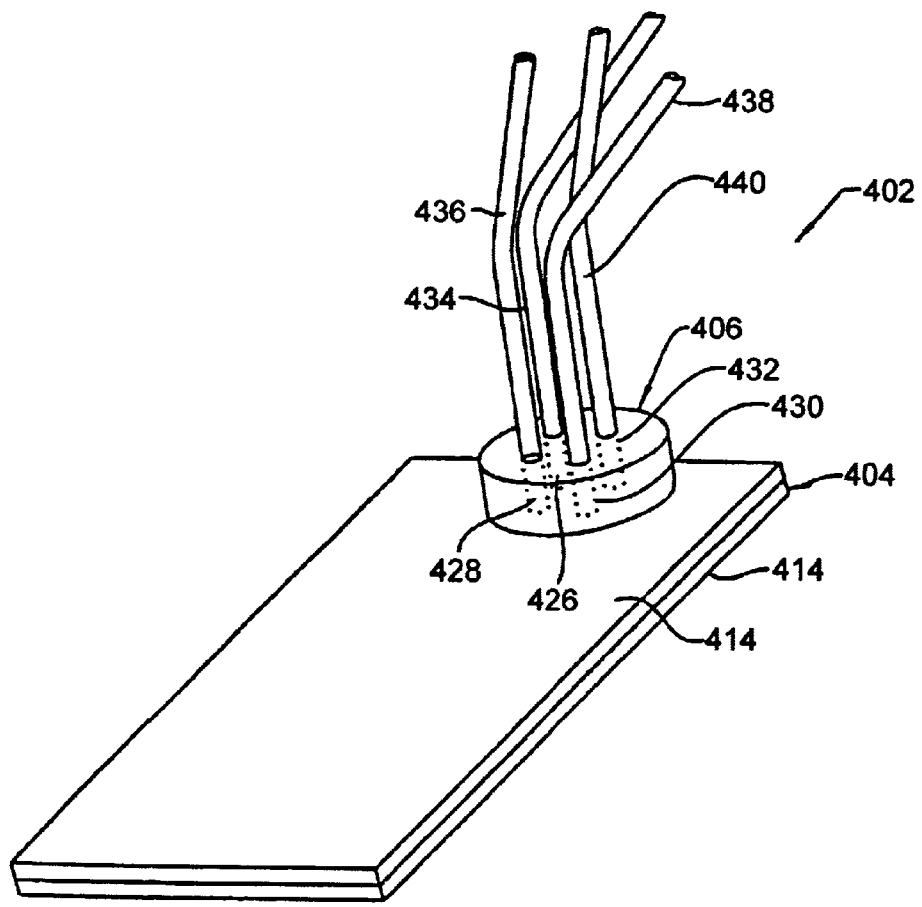
FIG. 17 is a pictorial representation of a liquid phase separation apparatus that includes the device of FIG. 16 and an externally arranged multi-position manifold means interfaced with the column device.
Figure 18A:
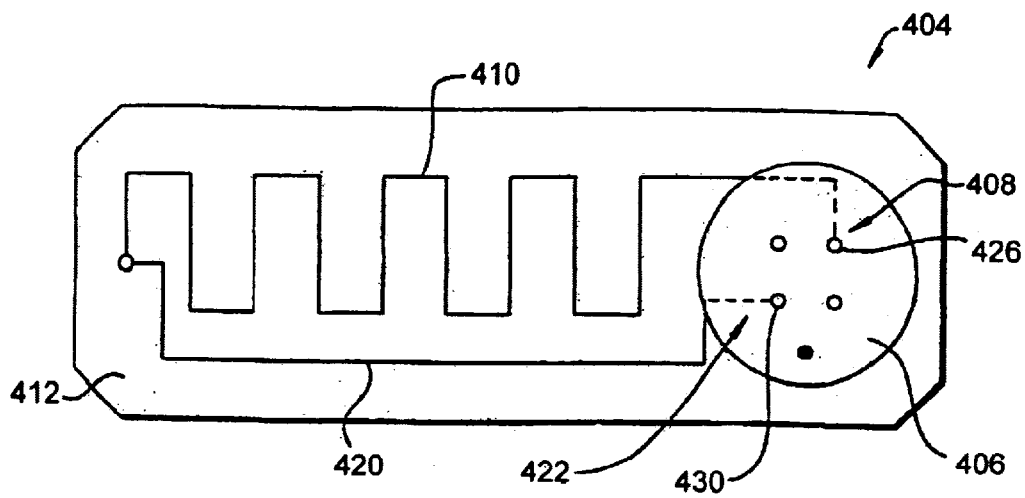
FIG. 18A is a pictorial representation of the apparatus of FIG. 17 with the manifold means arranged in a first position relative to the column device.

Referring particularly to FIG. 17, the manifold 406 includes a first port 426, a second port 428, a third port 430 and a fourth port 432, each port being configured to accept an associated conduit means 434, 436, 438, and 440, respectively. The conduit means are in fluid communication with associated fluid containment means (not shown), such that a fluid sample, reagent or buffer can be communicated to the various ports in the manifold 406 for delivery into the column device 404. Referring now to FIGS. 17 and 18A, when the manifold 406 is in a first position, the first manifold port 426 is in fluid communication with the upstream terminus 408 of the separation microchannel 410. In this position, a suitable liquid medium, such as an equilibrating buffer or a flush solution, can be delivered into the separation microcolumn (at the upstream terminus 408) from an associated containment means via the conduit means 434. Further, when the manifold is in the first position, the third manifold port 430 is in fluid communication with the upstream terminus of the makeup flow channel 420. Thus, a suitable liquid medium can be delivered into the makeup flow compartment (at the upstream terminus 422) from the same, or a different associated containment means, via the conduit means 438.

Figure 18B:
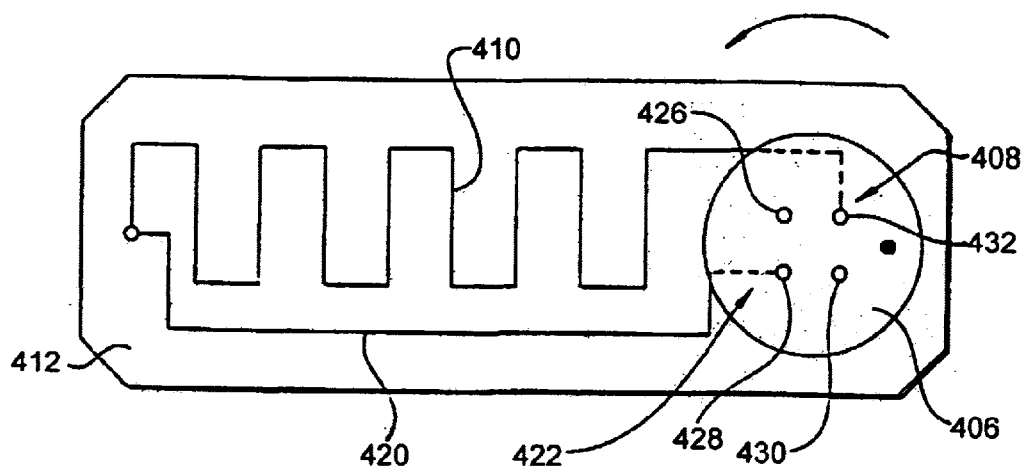
FIG. 18B is a pictorial representation of the apparatus of FIG. 17 with the manifold means arranged in a second position relative to the column device.
Figure 18C:
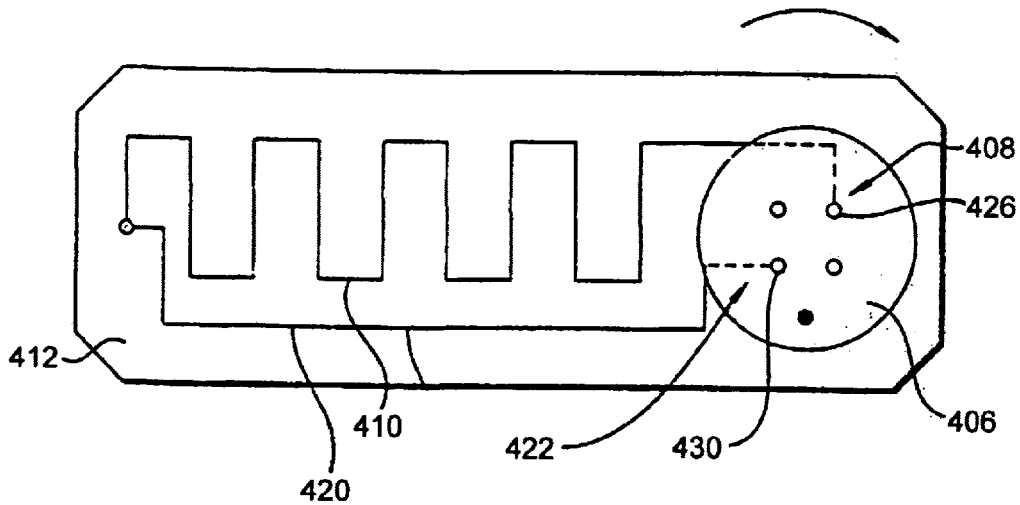
FIG. 18C is a pictorial representation of the apparatus of FIG. 17 with the manifold means returned to a first position relative to the column device.

Referring now to FIGS. 17 and 18B, when the manifold 406 has been rotated counter-clockwise about the stator to a second position relative the column device 404, the fourth manifold port 432 is brought into fluid communication with the upstream terminus 408 of the separation microchannel 410. Accordingly, a volume or aliquot of liquid sample can be delivered into the separation microcolumn (at the upstream terminus 408) from an associated sample containment means via the conduit means 440. When the manifold is arranged in the second position, the first and third manifold ports 426 and 430 are moved out of fluid communication with the separation microcolumn and the makeup fluid compartment such that liquid medium is no longer delivered into those compartments via conduit means 434 and 438. Further, in the second position, the second manifold port 428 is aligned to be in fluid communication with the upstream terminus 422 of the makeup fluid channel 420, and a liquid reagent, or a heated makeup fluid can be delivered into the makeup flow compartment (at the upstream terminus 422) from an associated sample containment means via the conduit means 436.

Accordingly, a liquid phase separation can be readily carried out using the apparatus 402, wherein the manifold 406 allows switching between a stand-by mode when the manifold is in the first position, and a separation mode when the manifold is in the second position. Alternatively, the above-described two position manifold can be used to alternate between a sample run position, corresponding to the manifold being arranged in the first position, and a sample loading position, corresponding to the manifold being arranged in the second position. The manifold 406 is switched to the second position (e.g., the position depicted in FIG. 18B) to deliver a particular volume of sample into the separation microcolumn. Once the sample has been delivered, the manifold is rotated clockwise about the stator to return to the first position relative the column device (e.g., the position depicted in FIG. 18C) in order to conduct liquid phase separation of the sample.

Further, as will be appreciated by those skilled in the art, movable, or multi-position manifolds, such as the manifold 406, can be coupled with any of the miniaturized column devices described herein to provide a liquid phase separation apparatus. Thus, such manifolds can be coupled to column devices which include on-device reservoirs, makeup fluid compartments, volumetric sample compartments and combinations thereof. In this manner, selective and/or temporal delivery of fluids from associated containment means into the various compartments of a miniaturized column is effected using the moveable manifolds described above.

The movable manifold can be configured in a wide variety of shapes, such as, but not limited to, an elongated finger-shaped housing or slide that is capable of either linear or rotational movement between a variety of positions, a circular or oval shaped housing capable of rotational movement between positions, or a semicircular housing that is capable of being rotated between a variety of positions. The manifold can also include any number of ports capable of communicating with an external conduit means, wherein two or more of the ports may also be capable of communicating with each other via lateral interconnecting port means. The configuration of the manifold and the layout of the ports will be generally dictated by the selected configuration of the separation microcolumn, the associated on-device compartments, the fluid conducting means, and the inlet ports and apertures that communicate with those elements.

A liquid phase separation apparatus may be provided having a movable manifold, wherein the manifold cooperates with an on-device volumetric sample compartment (e.g, a covered bypass channel in fluid communication with inlet and outlet means as described above), to enable the delivery of a sample plug of known volume from the sample compartment to the upstream terminus of a separation microcolumn. The manifold is detachably coupled to a miniaturized column device, and arranged in a first position such that external conduits disposed within two ports of the manifold enable dynamic fluid communication between the sample compartment (via the inlet and outlet means) and an associated sample containment means. A sample plug, having a volume corresponding to the dimensions of the volumetric sample compartment, is formed by the dynamic flow of sample through the compartment. By moving the manifold to a second position, different ports in the manifold are brought into fluid communication with the volumetric sample compartment inlet and outlet, whereby those ports allow the flow of an externally housed liquid medium through the sample compartment and into the separation microcolumn via associated conduits and/or lateral ports in the manifold. In this manner, the sample plug disposed within the volumetric sample compartment can be readily delivered to the separation microcolumn using known liquid injection techniques.

Figure 19:
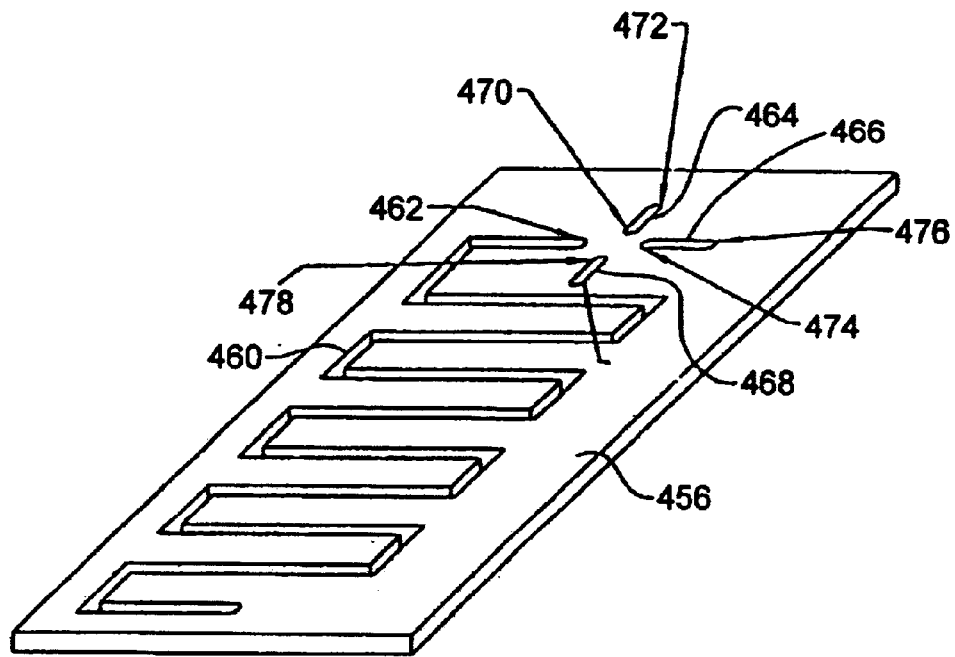
FIG. 19 is a plan view of a miniaturized column device having an alternative sample introduction means ablated or otherwise formed in a planar substrate.
Figure 20:
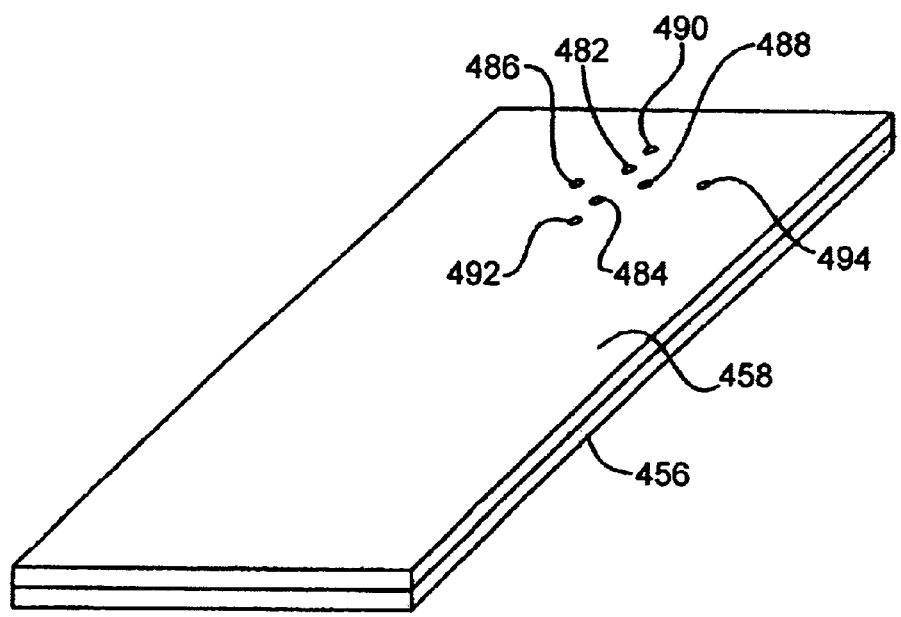
FIG. 20 is a plan view of the miniaturized column device of FIG. 19 having a cover plate aligned over the planar substrate.

An apparatus may also be provided having a movable manifold that includes an internal volumetric compartment. Referring now to FIGS. 19 and 20, a liquid phase separation apparatus is generally indicated at 452. The apparatus includes a miniaturized column device 454, having a substrate portion 456 and a cover plate 458. A separation microchannel 460 is laser ablated or otherwise fabricated in a planar surface of the substrate portion 456. The separation microchannel has an upstream terminus 462 disposed in close proximity to three discrete microchannels, 464, 466, and 468, that are also formed in the substrate portion 456. The microchannel 464 has a first and second terminus, respectively indicated at 470 and 472. Likewise, the microchannel 466 has a first and second terminus, 474 and 476, and the microchannel 468 has a first and second terminus 478 and 480.

A separation microcolumn is formed by arranging the cover plate 458 over the planar surface of the substrate portion 456. The cover plate includes a plurality of apertures that are arranged to provide fluid communication with the separation microcolumn and the microchannels 464, 466 and 468 when the cover plate is in place above the substrate. Specifically, laser ablated or otherwise fabricated apertures 482 and 490 are respectively in fluid communication with the first and second termini, 470 and 472, of the microchannel 464 to provide a first flow path. Laser ablated or otherwise fabricated apertures 484 and 492 are respectively in fluid communication with the first and second terminus, 478 and 480, of the microchannel 468 to provide a second flow path. A third flow path is provided by apertures 488 and 494, that are respectively in fluid communication with the first and second terminus, 474 and 476, of the microchannel 466. An aperture, 486, is in fluid communication with the upstream terminus 462 of the separation microchannel 460.

Figure 21:
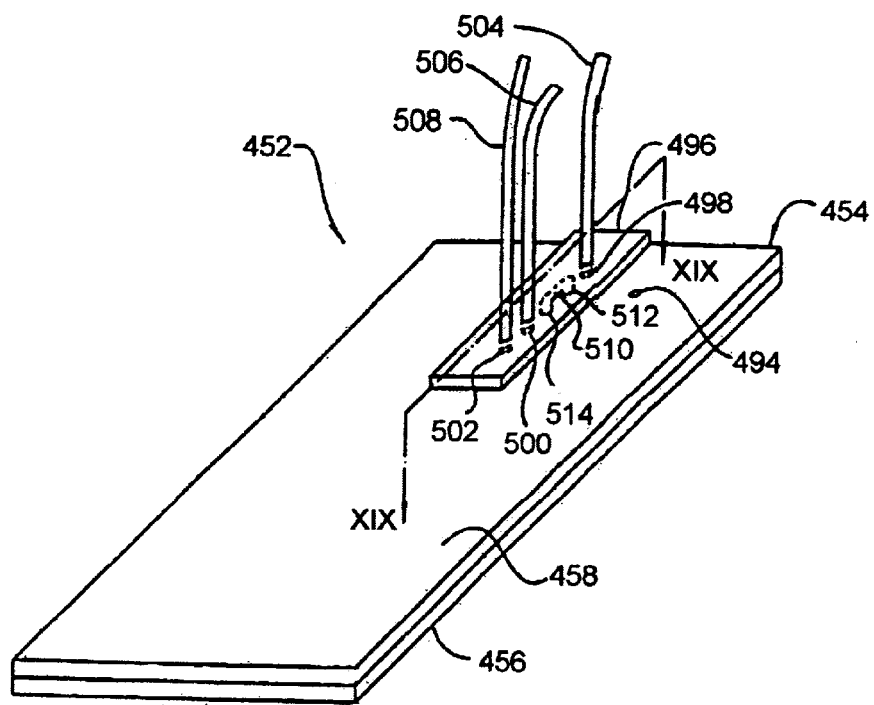
FIG. 21 is a pictorial representation of a liquid phase separation apparatus that includes the device of FIG. 20 and an externally arranged multi-position manifold means interfaced with the column device.
Figure 22:
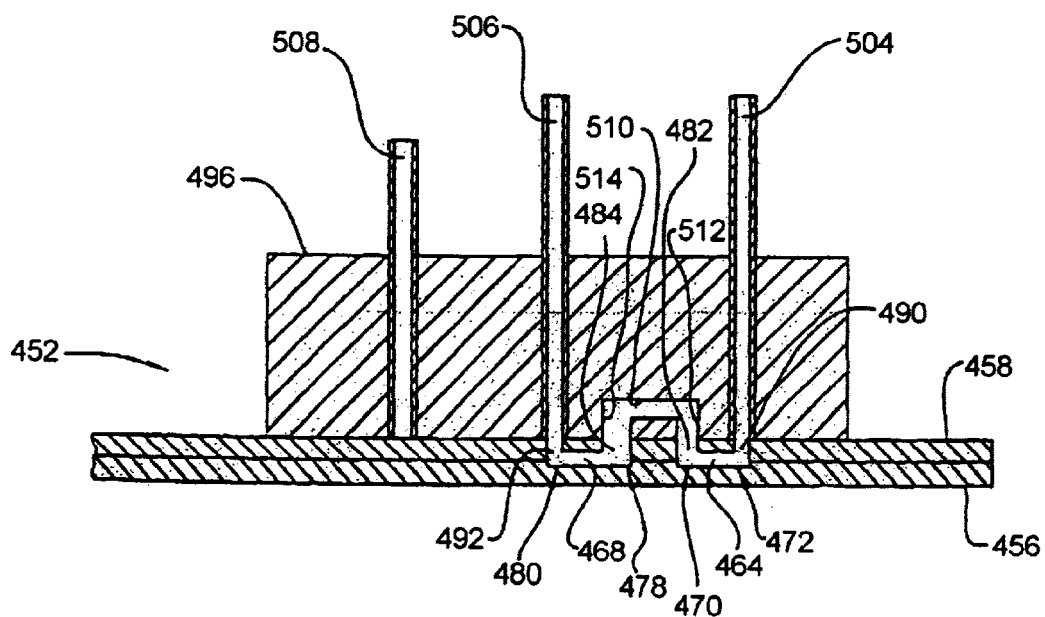
FIG. 22 is a cross-sectional view of the multi-position manifold of FIG. 21 taken along lines XIX—XIX.

Referring now to FIGS. 21 and 22, a movable manifold means 496 is coupled to the cover plate 458 to form a liquid-tight interface using known sealing techniques. Although the manifold means 496 is depicted in an elongated configuration, it is understood that the manifold can be provided in a large variety of suitable configurations as noted above. The manifold means 496 includes first, second and third ports, respectively indicated at 498, 500, and 502, wherein each port can cooperate with an external conduit means, respectively indicated at 504, 506 and 508. The manifold means 496 also includes an internal volumetric sample compartment 510, that comprises a generally U-shaped compartment having a first and second terminus, indicated at 512 and 514, respectively.

In a first position relative to the column device 454, the manifold 496 is arranged such that the manifold port 498 is in fluid communication with the aperture 490, the first terminus 512 of the internal sample compartment is in fluid communication with the aperture 482, the second terminus 514 of the internal sample compartment is in fluid communication with the aperture 484, and the manifold port 500 is in fluid communication with the aperture 492. In this first position, the manifold 496 enables one continuous flow path to be established when the conduit means 504 is communicated with an associated containment means housing a sample. Particularly, the sample is delivered to the microchannel 464 via the conduit means and passed to the volumetric sample compartment 510, continuing through the microchannel 468, and exiting the apparatus via the conduit means 506. Thus, a sample plug is formed within the volumetric sample compartment by the dynamic passage of sample therethrough.

Once a sample plug has been formed in the sample compartment 510, the manifold can be moved to a second position relative to the column device 454 by rotating the manifold counter-clockwise about a pivot (not shown) to bring the manifold port 502 into fluid communication with the aperture 494. Further, the second terminus 514 of the internal sample compartment is brought into fluid communication with the aperture 488, and the first terminus 512 of the internal sample compartment is brought into fluid communication with the aperture 486. In this position, the sample plug can be readily flushed from the volumetric sample compartment and into the separation microcolumn by passing a liquid medium from an external containment means through the manifold via the conduit means 508, whereby the medium passes through the aperture 494 to flow through the microchannel 466, continuing through the sample compartment 510, and passing through the aperture 486 to the upstream terminus 462 of the separation microchannel 460.

External hardware can be used to provide mechanical valving for divertable communication of various associated containment means containing, e.g., an electrolyte solution, flush solution or the liquid sample with the column device via the manifold means. Thus, a variety of injection methods can be used, including pressure injection, hydrodynamic injection or electrokinetic injection. The conduit means and any associated valving and injection means can communicate with the separation device through the manifold means, or communicate directly with the separation device by butt-coupling to apertures; however, any other suitable method of connection known in the art can be readily adapted to the invention. Further, it is noted that numerous other sample introduction and fluid interfacing designs can be practiced and still fall within the spirit of the subject invention.

Figure 23:
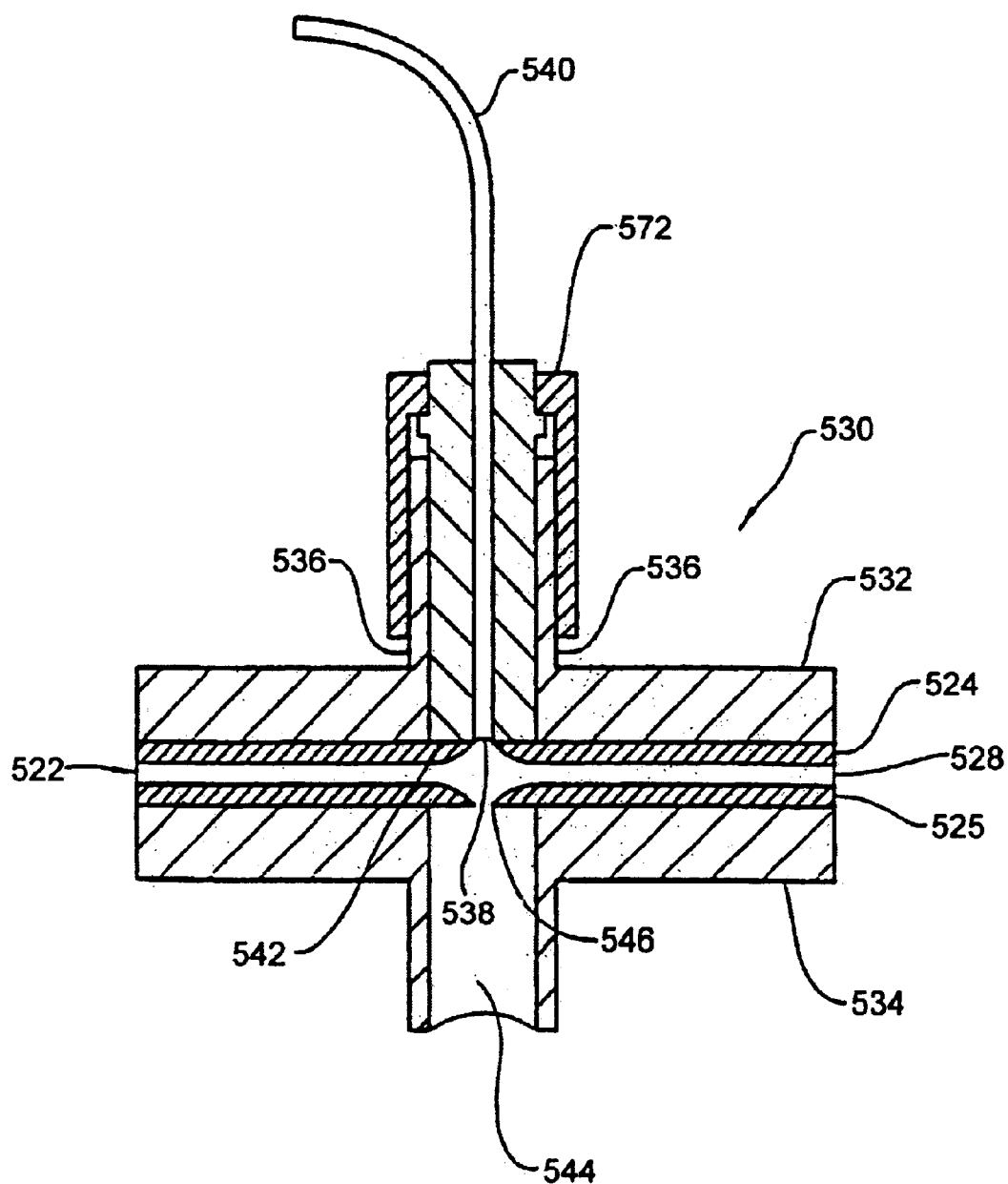
FIG. 23 is a cross-sectional view of a keeper means housing a miniaturized column device and enabling the interface of associated lightguide means with a detection means in the column device.

A liquid phase separation apparatus may also be provided having an associated keeper means that is adapted to receive and provide support to a miniaturized column device. Referring to FIG. 23, a miniaturized column 522 is depicted having first and second component halves 524 and 526. A separation microchannel 528 is provided by the alignment of corresponding channels that have been laser ablated or otherwise fabricated in each half to provide the mirror image of each other. The column 522 is supported by a keeper means 530 that generally comprises first and second opposable elements, 532 and 534, that are constructed to closely accept and provide structural support to the miniaturized column.

The keeper means can include optional means for facilitating the coupling of an associated conduit, lightguide or fastener with an aperture, inlet port, outlet port or detection means. Referring still to FIG. 23, the keeper means 530 includes an annular boss 536 that extends from the first opposable element 532. The annular boss is arranged to encircle an area including a detection means 538. The detection means 538 is formed from an aperture that has been laser ablated or otherwise fabricated in the component half 524 and communicates with the separation microcolumn 528. An associated lightguide means 540 is readily interfaced with the detection means 538 by the insertion of a distal end 540 thereof into the annular boss. A second annular boss, 544, extends from the second opposable element 534, and is arranged to encircle an area including a second detection means 546. The second detection means 546 is formed from an aperture that has been laser ablated or otherwise fabricated in the component half 526 and is arranged in coaxial alignment with the first detection means 538 to provide an optical detection path. A further lightguide means can thus be inserted into the second annular boss 544, whereby the contents of the separation microcolumn can be interrogated using associated optical detection means to detect separated analytes in the sample undergoing liquid phase analysis.

Although the annular bosses have been described herein in conjunction with coupling lightguide means with detection means, it will be appreciated by those skilled in the art that such means can be arranged in a plurality of locations about the keeper means to encircle inlets, outlets and apertures, whereby associated conduit means can be readily coupled to the devices to communicate fluids to and from the miniaturized columns.

Figure 24:
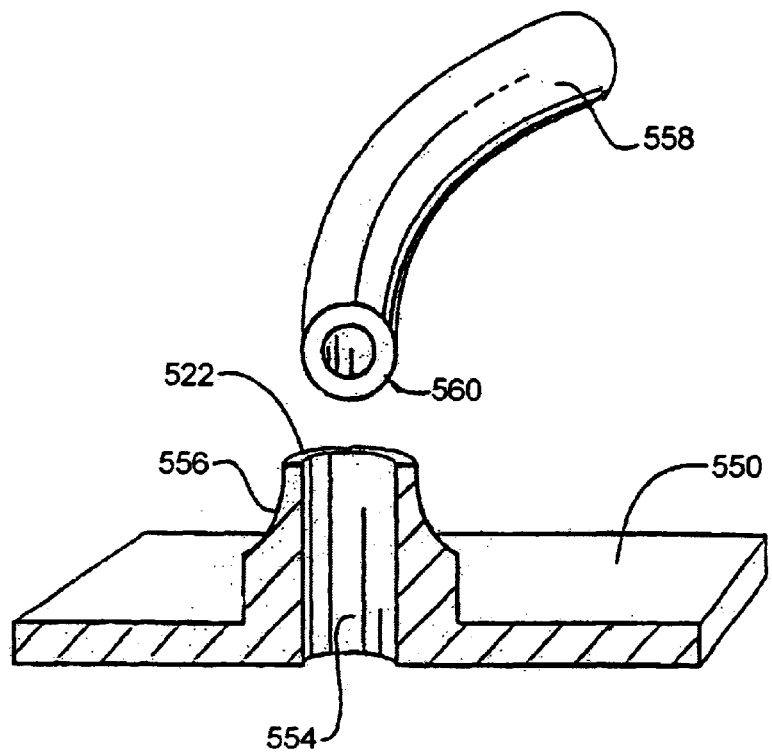
FIG. 24 is a pictorial representation of a keeper means having an annular boss that is adapted to cooperate with an associated conduit or lightguide means.

By providing annular bosses that have an inner diameter constructed within close tolerances, associated lightguide means or conduit means can be butt-coupled to the periphery of the column device 522 and frictionally held in place to provide a liquid-tight seal. Referring to FIG. 24, an opposable element 550 of a keeper means is depicted as having an annular boss 552 in the form of a projecting cylinder. The cylinder has an interior and an exterior surface, respectively indicated at 554 and 556. A distal terminus, 560, of an associated conduit means 558 can be inserted into the annular boss 552 and held in place as has been described above.

A keeper means may also be configured to have an optional lock means for detachably coupling a fastener, such as a conduit means or lightguide means, with an aperture, inlet, outlet or detection means on a miniaturized column. Referring to FIG. 23, the annular boss 536 is configured to cooperate with a closure 572. The closure comprises a sleeve that is disposed about the lightguide means 540. In practice, after the distal end 542 of the lightguide has been inserted into the annular boss, the closure 572 is slidably positioned about the periphery of the boss to provide a locking snap-fit in cooperation with the exterior surface of the annular boss 536.

The optional lock means can comprise machined threads arranged on the outer surface of an annular boss for threadably engaging mating threads arranged on the interior of a closure, such as a cap or the sleeve 572 depicted in FIG. 23. The threads enable an associated conduit means or lightguide means to be coupled to a miniaturized column device disposed within a keeper, and then locked into place to provide a superior liquid-tight seal.

Figure 25:
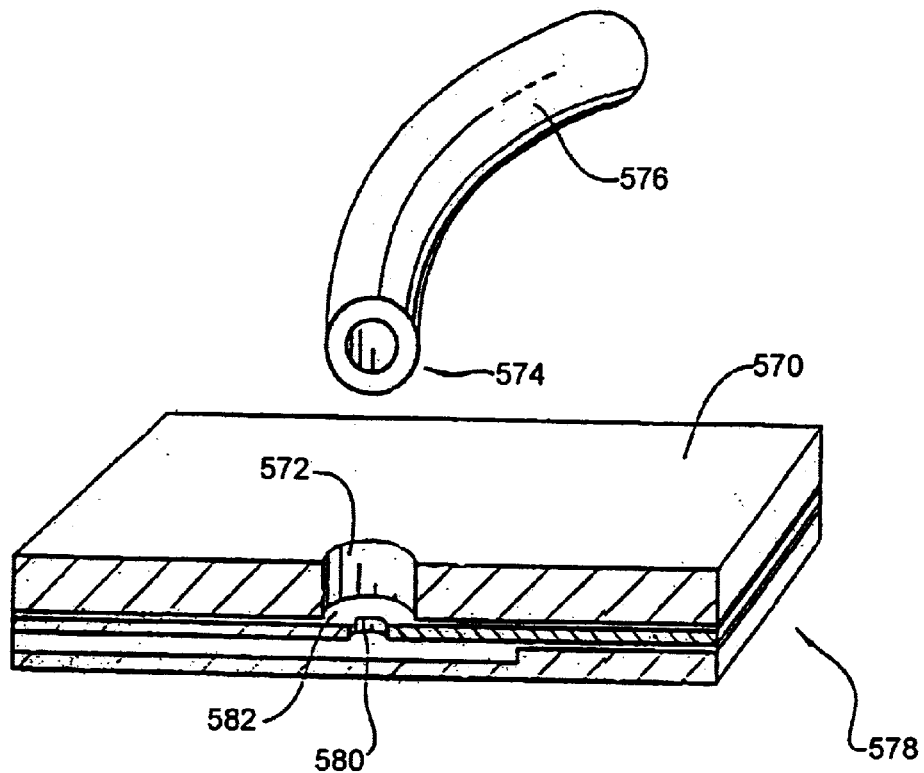
FIG. 25 is a pictorial representation of a keeper means having an aperture that is adapted to cooperate with an associated conduit or lightguide means.

An alternative keeper means may be provided having one or more apertures that facilitate the coupling of a fastener with an inlet port, outlet port, aperture or detection means in a miniaturized column. Referring now to FIG. 25, an opposable element 570 of a keeper means having an aperture 572 formed therein is depicted. The aperture is arranged in the keeper such that it encompasses an inlet port, aperture, detection means, or a like feature of a miniaturized column 578 that is disposed within the keeper. The distal end 574 of an associated conduit means 576 can be inserted into the aperture 572 and butt-coupled to the column device 578. Thus the aperture 572 can be sized to closely cooperate with the inserted conduit to resiliently maintain the coupling of the conduit to the column device, and to provide a liquid-tight seal.

In one particular configuration, the keeper aperture 572 is sized to have a greater diameter than that of the coaxially arranged column inlet port, outlet port or detection means. Referring still to FIG. 25, the keeper aperture 572 encompasses an aperture 580 in the miniaturized column device 578 that is disposed within the keeper means. The aperture 580 has a smaller diameter than that of the aperture 572. In this manner, a shoulder 582 is provided that serves as a sealing stop surface that cooperates with the distal end 574 of the inserted conduit means 576 to provide a liquid-tight seal. This particular configuration allows the conduit means to be urged to couple closely with the surface of the column device and provide a resilient liquid-tight seal, without the possibility of having the conduit means travel into the column device where it could interfere with the flow of liquids passing through the column device.

Accordingly, a number of liquid phase separation apparatus configurations have been described. It is to be understood that while the various elements of such configurations, such as the manifolds and rotors, keepers means, associated lightguide means and conduit means, have been described individually, it is expressly intended herein to combine such elements to provide a wide variety of apparatus configurations. Thus, keeper means used in the practice of the invention can be configured to cooperate with various manifold configurations, micropumps, actuators, and the like.

Figure 30:
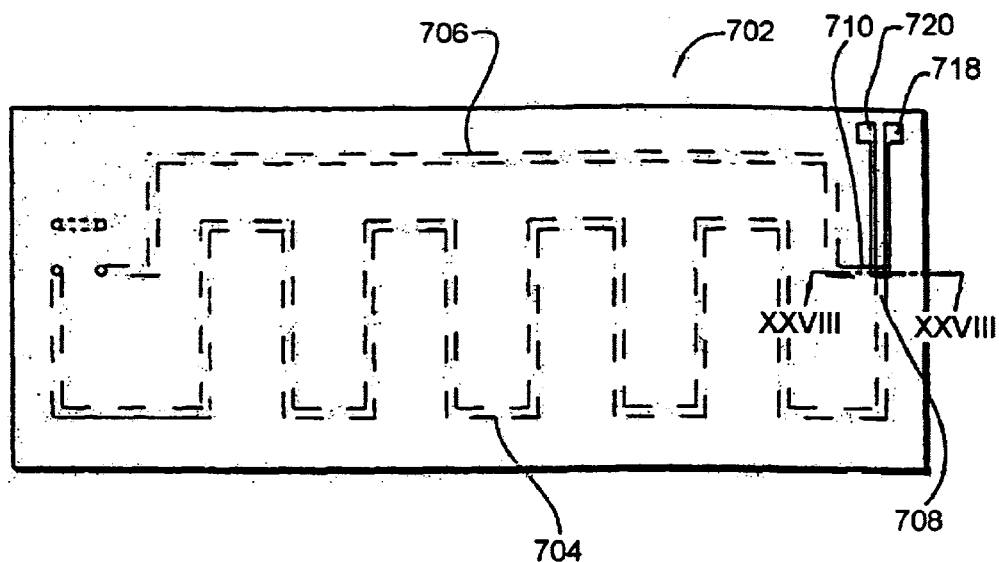
FIG. 30 is a plan view of a liquid phase separation apparatus having an alternative means for generating and expelling a sample eluate droplet that is actuated via electrical contacts.
Figure 31:
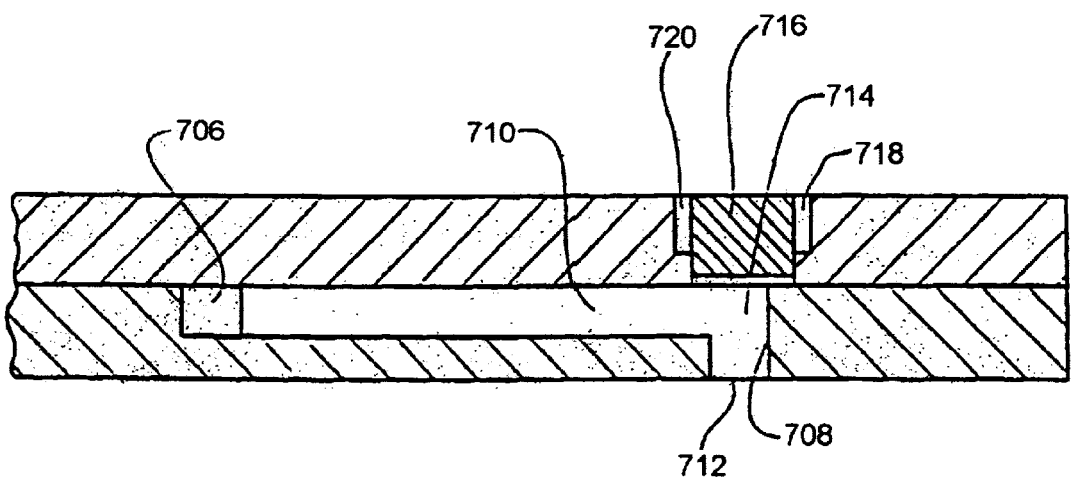
FIG. 31 is a cross-sectional representation of the apparatus of FIG. 30 taken along lines XXVIII—XXVIII.

In yet a further embodiment of the invention, a liquid phase separation apparatus is provided having means for assisting in the generation and expulsion of a sample eluate droplet from the separation microcolumn of a miniaturized column device. Referring to FIGS. 29–31, a miniaturized column 602 is shown that is formed from a substrate portion 604 and a cover plate portion 606 as has been described above. The column includes a separation microcolumn 608 having an upstream terminus 610 and a downstream terminus 612. An inlet port 614 is provided, and generally comprises an aperture arranged in the cover plate 606 to be in fluid communication with the upstream terminus 610 of the separation microcolumn when the cover plate is affixed above the substrate portion 604. An outlet port 616 is also provided, comprising an aperture formed in the substrate portion 604 that is in fluid communication with the downstream terminus 612 of the separation microcolumn. A flow path is formed that extends from the upstream terminus and travels along the length of the separation microcolumn to the downstream terminus. A liquid medium or sample housed in an associated containment means can be delivered to the upstream terminus 610 of the separation microcolumn by communicating a conduit from the containment means with the inlet port 614 via a manifold means or with the assistance of a keeper means as described above.

Figure 26:
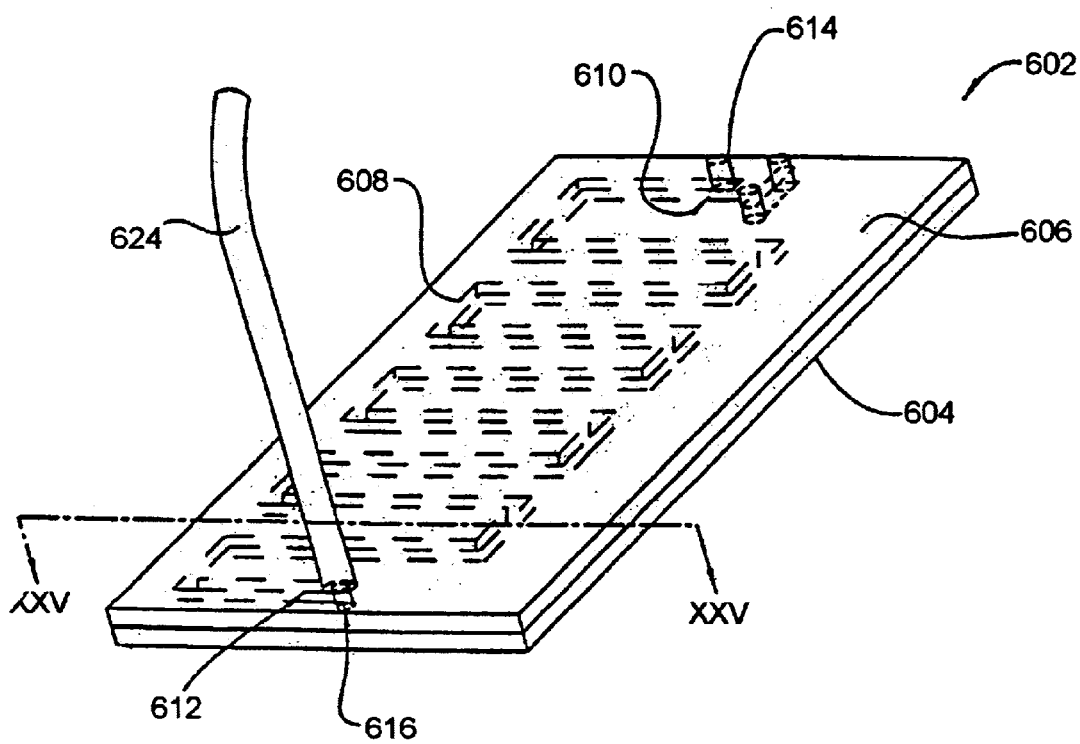
FIG. 26 is pictorial representation of an optional means for generating and expelling a sample eluate droplet from a liquid phase separation apparatus.
Figure 27:
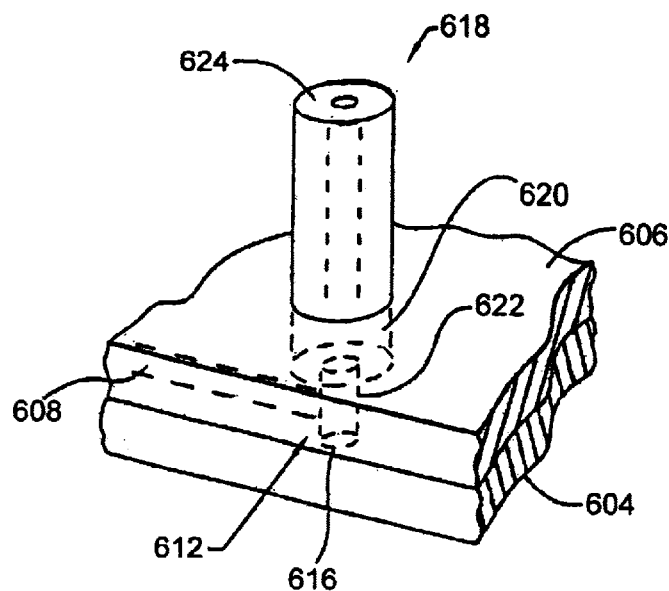
FIG. 27 is a pictorial representation of the interface of the means for generating and expelling a sample eluate droplet and the apparatus.
Figure 28:
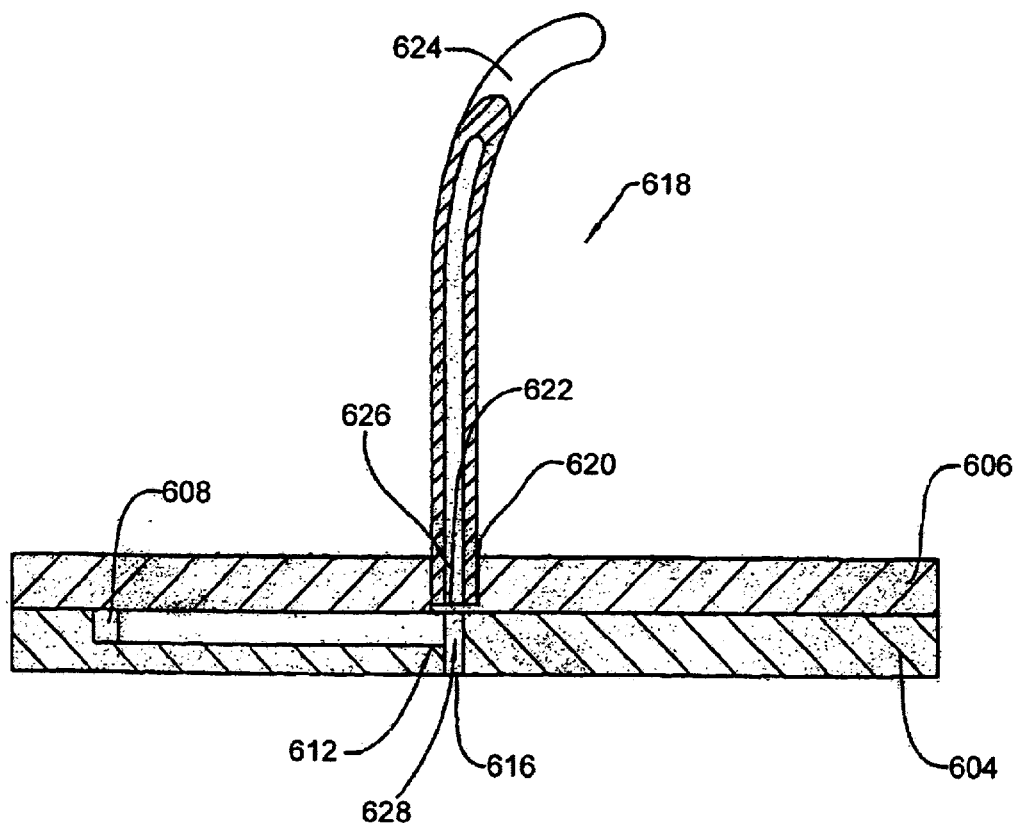
FIG. 28 is a cross-sectional view of the means for generating and expelling a sample eluate droplet of FIG. 23 taken along lines XXV—XXV.
Figure 29A:
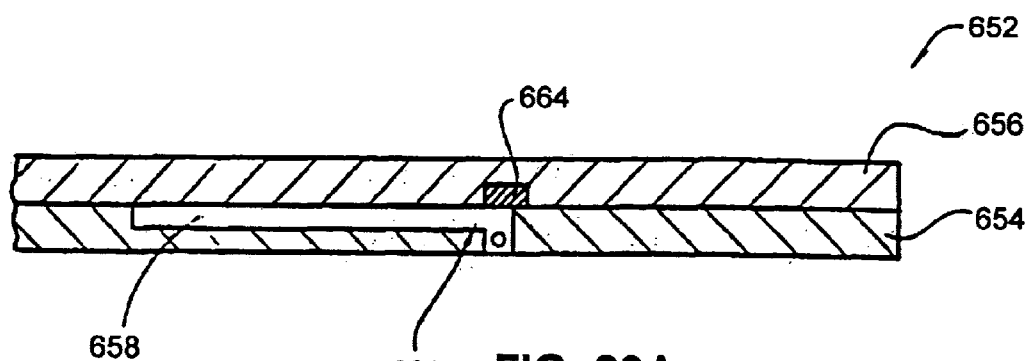
FIGS. 29A–29D are pictorial representations in cross section that depict the generation and expulsion of a sample eluate droplet from a liquid phase separation apparatus.
Figure 29B:
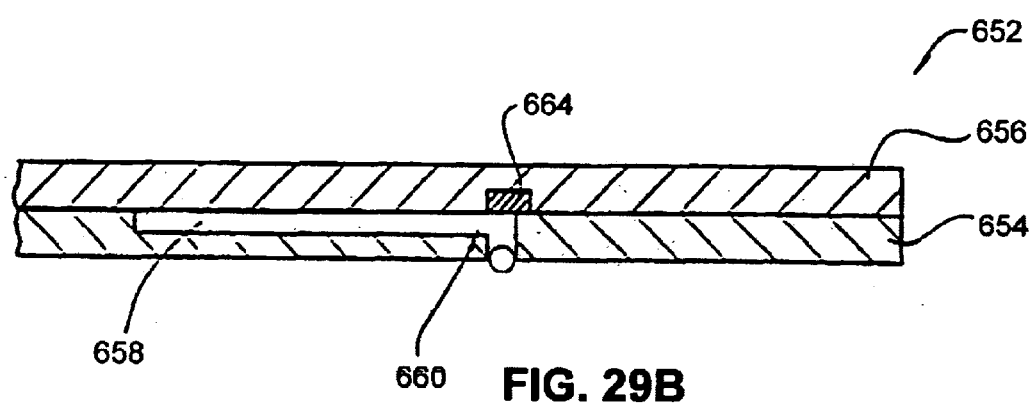
Figure 29C:
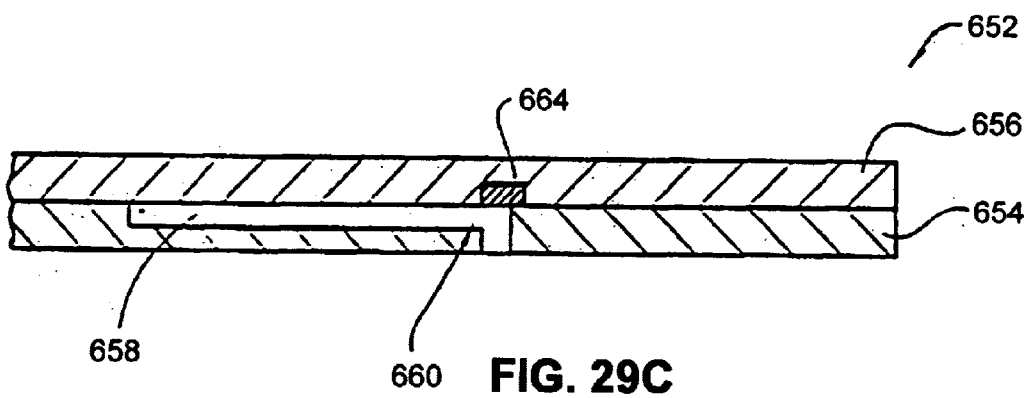
Figure 29D:
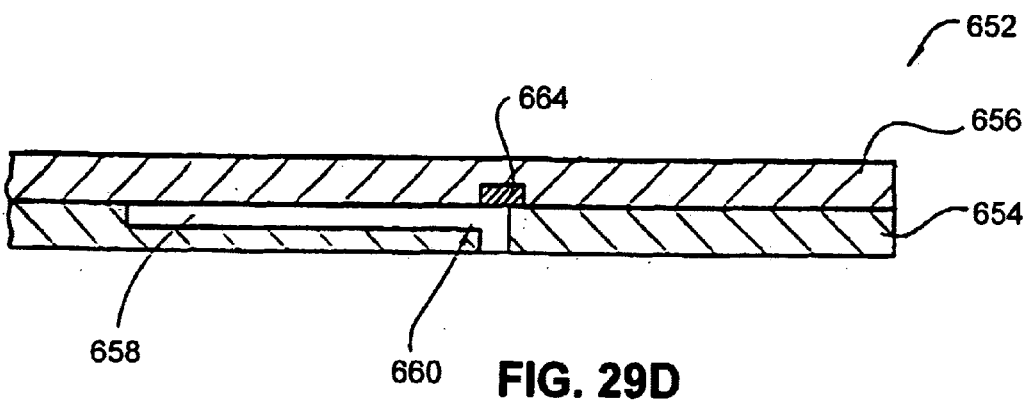

Referring still to FIGS. 26–28, the column device 602 also includes a sample eluate delivery means, generally indicated at 618, that is arranged adjacent to the downstream terminus 612 of the separation microcolumn. Specifically, the eluate delivery means 618 includes a recess 620 formed in the cover plate 606. An aperture 622 is disposed within the recess 620 and is arranged to be coaxially aligned and in fluid communication with the outlet port 616. The delivery means also includes an associated conduit means 624, wherein the distal end 626 is inserted into the recess 620 and butt-coupled to the aperture 622. An eluate from the separation microcolumn can be expelled from the outlet port by communicating an external pulsed air stream with the conduit means 624 to urge small fractions from the column by air pressure pulses, which fractions may then be collected using known techniques.

The conduit means can alternatively be interfaced with an external source of makeup fluids, enabling the communication of such fluids via the conduit means, through the aperture 622 and into contact with sample eluate emitting into the outlet port 616 from the downstream terminus 612 of the separation microcolumn 608. Referring to FIG. 28, this particular configuration provides a mixing chamber 628 which is formed from the intersection of the downstream terminus 612 of the separation microcolumn, the aperture 622 (which comprises a mixing chamber inlet means), and the outlet port 616. The outlet port 616 may optionally be tapered to provide an outlet nozzle. Droplets, containing a mixture of sample eluate and makeup fluid, are generated and expelled from the mixing chamber and may be collected using known techniques.

An alternative means for generating and expelling a sample eluate droplet from a miniaturized column device is shown in FIGS. 29A–29D. Specifically, a miniaturized column is indicated at 652. The column is formed from a substrate portion 654 and a cover plate portion 656, and includes a separation microcolumn 658 having a downstream terminus 660 in fluid communication with a sample delivery means 662, comprising an outlet port. A heating means 664 disposed within the cover plate 656 is arranged in thermal contact with the sample delivery means. By actuating the heating means, the temperature in the sample delivery means is increased. As the temperature increases, a steam bubble builds up in the sample delivery means 662, thereby forming sample droplet 668 which is expelled from the column device. For further discussion of fluid delivery using this method see Allen et al. (1985) Hewlett-Packard J. May 1985:21–27.

Yet another alternative means for generating and expelling a sample eluate droplet from a miniaturized column device is shown in FIGS. 30 and 31. As best seen in FIG. 30, a miniaturized column device 702 is provided having a separation microcolumn 704 and a makeup flow compartment 706 comprising channels that have been laser ablated or otherwise fabricated in the surface of a suitable planar substrate. Referring now to FIGS. 30 and 31, the separation microcolumn and the makeup flow compartment converge with a sample outlet nozzle 712 at their respective downstream termini, 708 and 710, to form a mixing chamber 714 wherein sample eluate exiting from the separation microcolumn 704 can intermix with makeup fluid exiting from the makeup flow compartment 706. A heating means 716 is situated in thermal contact with the mixing chamber 714. As described above, actuation of the heating means 716 results in the increase in the temperature thereof, the build up of a steam bubble in the mixing chamber 714, and the formation and expulsion of a sample eluate droplet. In one particular configuration, the heating means comprises a resistor type heating element that is actuated via first and second electrical contacts 718 and 720 using an associated source of electrical power.

Figure 32:
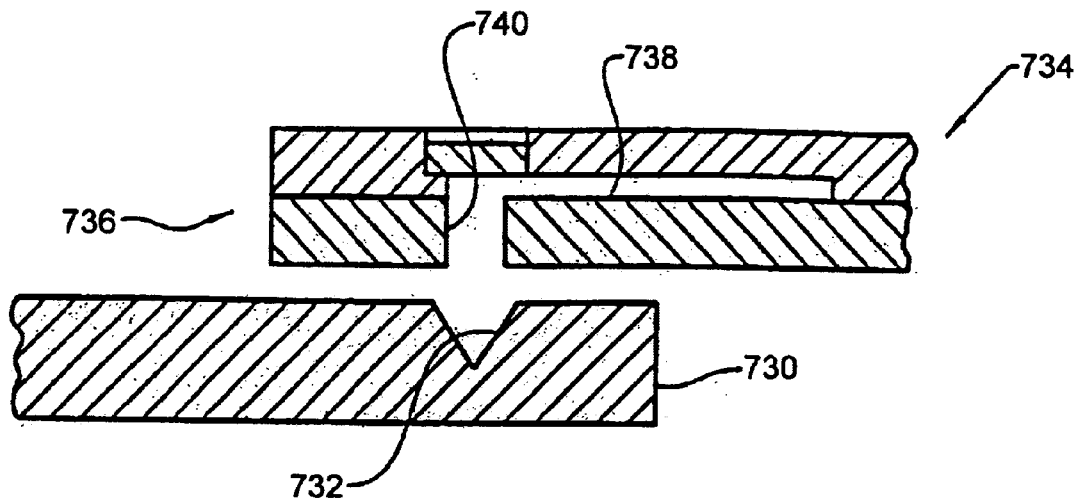
FIG. 32 is a pictorial representation in cross section of optional means for collecting a sample eluate droplet from a miniaturized column device or liquid phase separation apparatus.

In each of the above-described embodiments, an optional post-column collection means can be positioned relative to an outlet port or outlet nozzle to collect sample eluate exiting from the separation microcolumn. Referring to FIG. 32, a post-column collection device 730 (shown in cross-section) may be a substrate in which sample eluate droplet receiving microwell 732 has been laser ablated or otherwise fabricated. As described with respect to other microstructures formed by laser ablation, microwell 732 may be of any geometry and any aspect ratio.

Figure 33:
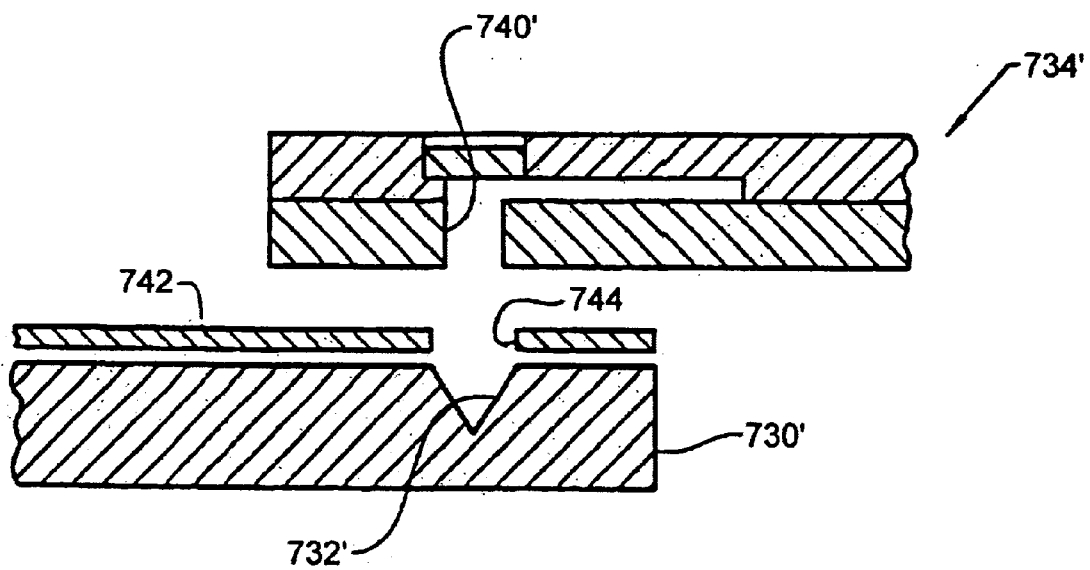
FIG. 33 is a pictorial representation in cross section of an alternative means for collecting a sample eluate droplet from a miniaturized column device or liquid phase separation apparatus.

More specifically, the collection device 730 is positioned relative to the distal end 736 of a miniaturized column device 734 such that sample eluate drops emanating from a separation microcolumn 738 and passing through an outlet port 740 can be collected for post-separation analysis or for further manipulations. Referring now to FIG. 33, a post-column collection device 730' (also shown in cross-section) may be a substrate in which sample droplet receiving microwell 732' has been laser ablated or otherwise fabricated. In addition, protective plate 742 can be removably interposed between the column device 734' and the post-column collection device 730'. The protective plate 742 generally comprises a structure having an opening 744 that is arranged to be in axial alignment with the outlet port 740' and receiving well 732' and is intended to provide protection of empty or filled wells from contamination or from evaporation of sample droplets previously collected.

Figure 34:
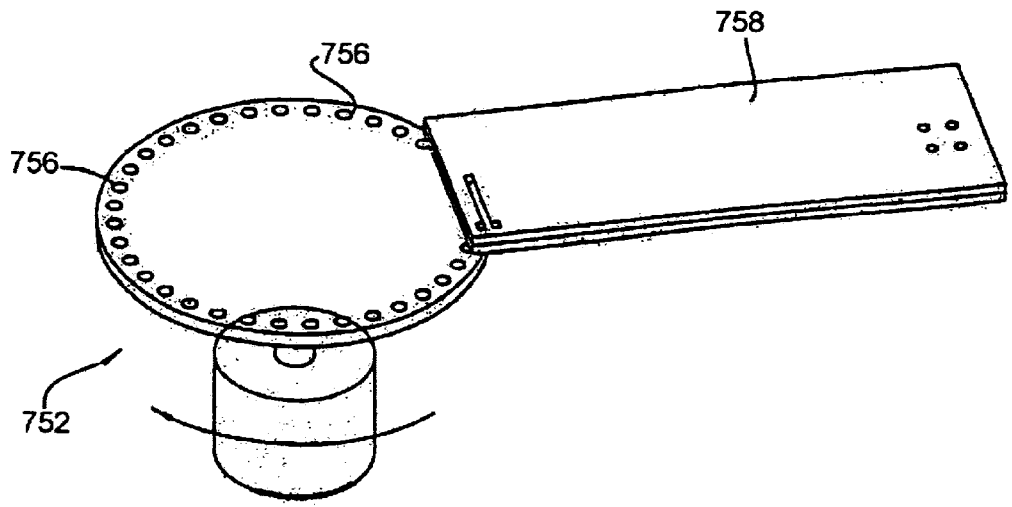
FIG. 34 is a pictorial representation of an alternative means for collecting a sample eluate droplet from a miniaturized column device or liquid phase separation apparatus, wherein the sample collection means is rotatable relative to the device or apparatus.
Figure 35:
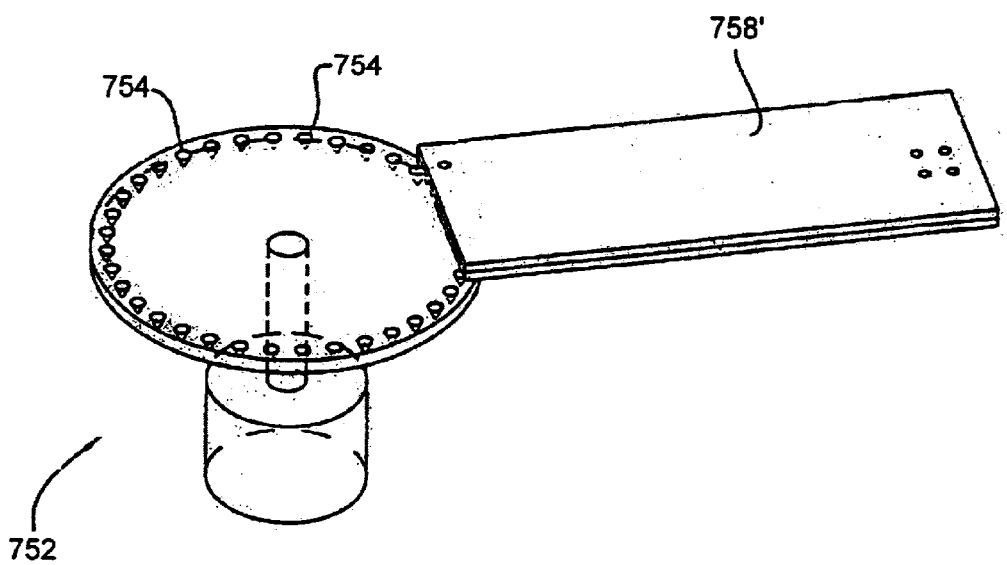
FIG. 35 is a pictorial representation of the sample collection means of FIG. 34 comprising optional sample collection microwells.

Referring now to FIGS. 34 and 35, a post-column collection device 752 comprising sample receiving means that may be sample receiving wells 754 or bibulous sheet means 756 is positioned relative to the outlet port of a miniaturized column device 758 or 758' to receive sample eluate droplets emitted from the column. Referring to FIG. 35, the sample receiving means can preferably be one or more microwells 754 laser ablated or otherwise fabricated in a substrate for liquid phase sample collection. Alternatively, the sample receiving means can be one or more bibulous sheet means 756 for solid-phase sample collection as shown in FIG. 34. The substrate used in the construction of the post-column collection device 752 is optionally a material other than silicon or silicon dioxide wherein microwells 754 can be laser ablated or otherwise fabricated in the substrate.

As shown in FIGS. 34 and 35, the receiving means can preferably be in rotatable alignment with the outlet port of the miniaturized column 758 or 758' such that multiple fractions may be collected. Further, as described above, the post-column collection device 752 can include a protection means having an opening that is arranged to be in axial alignment with the outlet port of the column device, wherein the protection means is interposed between the miniaturized column 758 or 758' and the sample receiving means. Although the post-column collection device 752 has been depicted herein as a disc in rotatable alignment with column device 758, it will be recognized by one of skill in the art that the configuration of the collection device need not be so limited. Thus, the post-column collection device 752 may be configured, for example, as a linear arrangement of sample receiving wells 754, or the like.

Further, while the present invention has been described with reference to specific preferred embodiments, it is understood that the description and examples included herein are intended to illustrate and not limit the scope of the invention, which is defined by the scope of the appended claims.

What is claimed is:

1. A microanalytical device in which chemical and biochemical reactions can be conducted, comprising:

a substrate fabricated from materials that are not silicon based, said substrate having first and second substantially planar opposing surfaces, and said substrate having a cavity and at least one microchannel formed in the first planar surface, wherein the cavity serves as a reaction zone that is in fluid communication with each microchannel;

a cover plate arranged over the first planar surface, said cover plate in combination with the cavity defining a reaction chamber, and with each microchannel defining a microcolumn; and at least one inlet port and at least one outlet port communicating directly or indirectly with the reaction chamber, said ports enabling the passage of fluid from an external source into and through the reaction chamber, thereby defining a fluid flow path;

wherein a surface of the reaction chamber and/or the microcolumn is coated with or functionalized to contain a polyether.

2. The microanalytical device of claim 1, wherein the substrate is comprised of material that provides for reduced sorption of solutes compared to a substrate formed from a silicon-containing material.

3. The microanalytical device of claim 1, wherein the substrate material is polymeric.

4. The microanalytical device of claim 3, wherein the substrate material is selected from the group consisting of polyimides, polycarbonates, polyesters, polyamides, polyethers, polyurethanes, polyfluorocarbons, polystyrenes, poly(acrylonitrile-butadiene-styrene), polymethyl methacrylate, polyolefins, and copolymers thereof.

5. The microanalytical device of claim 4, wherein the substrate is comprised of polyimide.

6. The microanalytical device of claim 5, wherein the polyether is a polyethylene oxide.

7. The microanalytical device of claim 3, wherein the polyether is a polyethylene oxide.

8. The microanalytical device of claim 1, further including an additional cavity formed in the first planar surface, which in combination with the cover plate forms an additional reaction chamber.

9. The microanalytical device of claim 1, wherein the reaction chamber has an upstream region in which fluid is introduced and a downstream region from which fluid exits, and wherein the at least one microchannel comprises an upstream microchannel in fluid communication with the upstream region of the reaction chamber and a downstream microchannel in fluid communication with the downstream region of the reaction chamber.

10. The microanalytical device of claim 9, wherein the upstream microchannel in combination with the cover plate forms an upstream microcolumn, and the downstream microchannel in combination with the cover plate forms a downstream microcolumn.

11. The microanalytical device of claim 1, further including motive means to move fluid through the fluid flow path.

12. The microanalytical device of claim 11, wherein the motive means comprises a means for applying a voltage differential.

13. The microanalytical device of claim 11, wherein the motive means comprises a means for applying a pressure differential.

14. The microanalytical device of claim 1, wherein the reaction chamber is sized to contain approximately 1 $\mu$l to 500 $\mu$l of fluid.

15. The microanalytical device of claim 14, wherein the reaction chamber is sized to contain approximately 10 $\mu$l to 200 $\mu$l of fluid.

16. The microanalytical device of claim 1, wherein the at least one microchannel is approximately 1 $\mu$m to 200 $\mu$m in diameter.

17. The microanalytical device of claim 16, wherein the at least one microchannel is approximately 10 $\mu$m to 75 $\mu$m in diameter.

18. A method for conducting a chemical or biochemical reaction with small amounts of fluid, comprising:
   (a) introducing a reaction fluid into a microanalytical device comprising
       a substrate fabricated from materials that are not silicon based, said substrate having first and second substantially planar opposing surfaces, and said substrate having a cavity and at least one microchannel formed in the first planar surface, wherein the cavity serves as a reaction zone that is in fluid communication with each microchannel.
       a cover plate arranged over the first planar surface, said cover plate in combination with the cavity defining a reaction chamber, and with each microchannel defining a microcolumn; and
       at least one inlet port and at least one outlet port communicating directly or indirectly with the reaction chamber, said ports enabling the passage of fluid from an external source into and through the reaction chamber, thereby defining a fluid flow path,
       wherein a surface of the reaction chamber and/or the microcolumn is coated with or functionalized to contain a polyether;
   (b) applying a motive force to the device to move the reaction fluid through the flow path; and
   (c) conducting the desired reaction when the reaction fluid is in the reaction chamber, resulting in a reaction product.

19. The method of claim 18, wherein step (c) is conducted by heating the reaction chamber.

20. The method of claim 18, further including collecting the reaction product at the outlet port.

* * * * *